US008563002B2

(12) United States Patent  
Baudoux et al.

(10) Patent No.: US 8,563,002 B2  
(45) Date of Patent: Oct. 22, 2013

(54) RECOMBINANT RSV ANTIGENS

(75) Inventors: Guy Jean Marie Fernand Pierre Baudoux, Rixensart (BE); Normand Blais, Lava (CA); Patrick Rheault, Laval (CA); Jean-Louis Ruelle, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 282 days.

(21) Appl. No.: 12/810,196

(22) PCT Filed: Dec. 23, 2008

(86) PCT No.: PCT/CA2008/002277  
§ 371 (c)(1),  
(2), (4) Date: Jun. 23, 2010

(87) PCT Pub. No.: WO2009/079796  
PCT Pub. Date: Jul. 2, 2009

(65) Prior Publication Data  
US 2010/0291147 A1    Nov. 18, 2010

Related U.S. Application Data

(60) Provisional application No. 61/016,524, filed on Dec. 24, 2007, provisional application No. 61/056,206, filed on May 27, 2008.

(51) Int. Cl.  
*A61K 39/00* (2006.01)  
*A61K 39/295* (2006.01)  
*A61K 39/155* (2006.01)

(52) U.S. Cl.  
USPC .................. 424/192.1; 424/201.1; 424/211.1; 435/5

(58) Field of Classification Search  
None  
See application file for complete search history.

(56) References Cited

U.S. PATENT DOCUMENTS

| | | | |
|---|---|---|---|
| 4,436,727 A | 3/1984 | Ribi | |
| 4,866,034 A | 9/1989 | Ribi | |
| 4,877,611 A | 10/1989 | Cantrel | |
| 4,912,094 A | 3/1990 | Myers | |
| 5,057,540 A | 10/1991 | Kensil et al. | |
| 5,149,650 A | 9/1992 | Wertz et al. | |
| 5,194,595 A | 3/1993 | Wathen | |
| 5,750,110 A | 5/1998 | Prieels et al. | |
| 5,776,468 A | 7/1998 | Hauser et al. | |
| 6,113,911 A | 9/2000 | Binz et al. | |
| 7,357,936 B1 | 4/2008 | Garcon et al. | |
| 7,368,537 B2 | 5/2008 | Anderson et al. | |
| 2008/0300382 A1 | 12/2008 | Libon et al. | |
| 2010/0261155 A1* | 10/2010 | Peeples et al. | 435/5 |
| 2011/0177117 A1 | 7/2011 | Blais et al. | |
| 2011/0206758 A1 | 8/2011 | Vandepapeliere et al. | |
| 2012/0093847 A1 | 4/2012 | Baudoux et al. | |
| 2012/0135028 A1 | 5/2012 | Blais et al. | |

FOREIGN PATENT DOCUMENTS

| | | |
|---|---|---|
| EP | 0109942 | 3/1991 |
| EP | 0362279 | 1/1995 |
| GB | 2220211 | 1/1990 |
| WO | WO 89/05823 | 6/1989 |
| WO | WO 94/15968 | 12/1994 |
| WO | WO 96/11711 | 4/1996 |
| WO | WO 96/33739 | 10/1996 |
| WO | WO 99/14334 | 3/1999 |
| WO | WO 02/42326 | 5/2002 |
| WO | WO 2006/038131 | 4/2006 |
| WO | WO 2008/114149 | 9/2008 |

OTHER PUBLICATIONS

Brideau, et al., "A chimeric glycoprotein of human respiratory syncytial virus termed FG induces T-cell mediated immunity in mice", Vaccine 9(12):863-864 (1991).

Calder, et al., "Electron microscopy of the human respiratory syncytial virus fusion protein and complexes that it forms with monoclonal antibodies", Virology, 271:122-131 (2000).

Connolly, et al, "Refolding a paramyxovirus F protein form prefusion to postfusion conformations observed by liposome binding and electron microscopy", Proceedings of the National Academy of Sciences of the United States, 103:17903-17908 (2006).

Connors, et al., "Cotton rats previously immunized with a chimeric RSV FG glycoprotein develop enhanced pulmonary pathology when infected with RSV, a phenomenon not encountered following immunization with vaccinia—RSV recombinants or RSV", Vaccine 10(7):475-484 (1992).

Ewasyshyn, et al., "Comparative analysis of the immunostimulatory properties of different adjuvants on the immunogenicity of a prototype parainfluenza virus type 3 subunit vaccine", Vaccine, 10(6):412-420 (1992).

Harbury, et al., "A switch between two-, three-, and four-stranded coiled coils in GCN4 leucine zipper mutants", Science, 262:1401-1407 (1993).

Mejias, et al., "New Approaches to reduce the burden of RSV infection", Drug Discovery Today: Therapeutic Strategies, 3(2):173-181 (2006).

Morton, et al., "Structural characterization of respiratory syncytial virus fusion inhibitor escape mutants: homology model of the F protein and a syncytium formation assay", Virology, 311:275-288 (2003).

Olmstead, et al., "Expression of the F glycoprotein of respiratory syncytial virus by a recombinant vaccinia virus: Comparison of the individual contributions of the F and G Glycoproteins to host immunity", Proceedings of the National Academy of Sciences of the United States, 83:7462-7466 (1986).

(Continued)

*Primary Examiner* — Stacy B. Chen  
(74) *Attorney, Agent, or Firm* — Gwynedd Warren; GlaxoSmithKline Global Patents Dept

(57) ABSTRACT

This disclosure provides recombinant respiratory syncytial virus (RSV) antigens and methods for making and using them, including immunogenic compositions (e.g., vaccines) for the treatment and/or prevention of RSV infection.

20 Claims, 10 Drawing Sheets

(56) References Cited

OTHER PUBLICATIONS

Olson, et al., "Pulmonary immunity and immunopathology: lessons from respiratory syncytial virus", Expert Review of Vaccines, 7(8):1239-1255 (2008).
Sakurai, et al., "Human antibody responses to mature and immature forms of viral envelope in respiratory syncytial virus infection: significance for subunit vaccines", Journal of Virology, 73(4):2956-2692 (1999).
Van Drunen Little-van den Hurk, et al., "Immunopathology of RSV infection: prospects for developing vaccines without this complication", Reviews in Medical Virology, 17(1):5-34 (2007).
Walsh, et al., "Immunization with glycoprotein subunits of respiratory syncytial virus to protect cotton rats against viral infection", J. Infect. Dis., 155:1198-1204 (1987).
Yin, et al., "Structure of the uncleaved ectodomain of the paramyxovirus (hPIV3) fusion protein", Proceedings of the National Academy of Sciences of the United States, 102(26):9288-9293 (2005).
Zhang, et al., "Signal peptide prediction based on analysis of experimentally verified cleavage sites", Protein Sci., 13:2819-2824 (2004).
Zimmer, et al., "Cleavage at the furin consensus sequence RAR/KR109 and presence of the intervening peptide of the Respiratory Syncytial Virus fusion protein are dispensable for virus replication in cell culture", J. Virol. 76:9218-9224 (2002).
Zimmer, et al., "Proteolytic activation of Respiratory Syncytial Virus fusion protein", J. Biol. Chem. 276:31642-31650 (2001).
Huang, et al., "Modulation of protective immunity, eosinophilia, and cytokine responses by selective mutagenesis of a recombinant G protein vaccine against respiratory syncytial virus", *Journal of Virology*, 79:4527-4532 (2005).
Valarcher, et al., "Bovine respiratory syncytial virus lacking the virokinin or with a mutation in furin cleavage site RA(R/K)R$^{109}$ induces less pulmonary inflammation without impeding the induction of protective immunity in calves", *Journal of General Virology*, 87(6):1659-1667 (2006).
Martin, et al., "Sequence elements of the fusion peptide of human respiratory syncytial virus fusion protein required for activity", *Journal of General Virology*, 87(6):1649-58 (2006).
Gonzalez-Reyes, et al., "Cleavage of the human respiratory syncytial virus fusion protein at two distinct sites is required for activation of membrane fusion", *Proceedings of the National Academy of Science USA*, 98(7):9859-64 (2001).
Yin, et al., "Structure of the parainfluenza virus 5 F protein in its metastable, prefusion conformation", *Nature*, 439(7072):38-44 (2006).
Schmidt, et al., "Mucosal immunization of rhesus monkeys against respiratory syncytial virus subgroups A and B and human parainfluenza virus type 3 by using a live cDNA-derived vaccine based on a host range-attenuated bovine parainfluenza virus type 3 vector backbone", *Journal of Virology*, 76(3):1089-99 (2002).
Tang, et al., "Parainfluenza virus type 3 expressing the native or soluble fusion (F) protein of respiratory syncytial virus (RSV) confers protection from RSV infection in African green monkeys", *Journal of Virology*, 78(20):11198-11207 (2004).
Bembridge, et al., "Priming with a secreted form of the fusion protein of respiratory syncytial virus (RSV) promotes interleukin-4 (IL-4 and IL-5) production by not pulmonary eosinophilia following RSV challenge", Journal of Virology, 73(12):100-86-10094 (1999).
Bolt, et al., "Cleavage of the respiratory syncytial virus fusion protein is required for its surface expression: role of furin", Virus Research, 68:25-33 (2000).
Falsey, et al., "Comparison of the safety and immunogenicity of 2 respiratory syncytial virus (RSV) vaccines—nonadjuvanted vaccine or vaccine adjuvanted with alum—given concomitantly with influenza vaccine to high-risk elderly individuals" The Journal of Infectious Diseases, 198:1317-1326 (2008).
Hancock, et al., "Generation of atypical pulmonary inflammatory responses in BALB/c mice after immunization with the native attachment (G) glycoprotein of respiratory syncytial virus", Journal of Virology, 70(11):7783-7791 (1996).
Hancock, et al., "Serum neutralizing antibody titers of seropositive chimpanzees immunized with vaccines coformulate with natural fusion and attachment proteins of respiratory syncytial virus", The Journal of Infectious Diseases, 181:1768-1771 (2000).
Matthews, et al., "The core of the respiratory syncytial virus fusion protein is a trimeric coiled coil", Journal of Virology, 74(13):5911-5920 (2000).
Piedra, et al., "Immunogenicity of a new purified fusion protein vaccine to respiratory syncytial virus: a multi-center trial in children with cystic fibrosis", Vaccine, 21:2448-2460 (2003).
Prince, et al., "Efficacy and safety studies of a recombinant chimeric respiratory syncytial virus FG glycoprotein vaccine in cotton rats", Journal of Virology, 74(22):10287-10292 (2000).
Ruiz-Arguello, et al., "Effect of proteolytic processing at two distinct sites on shape and aggregation of an anchorless fusion protein of human respiratory syncytial virus and fate of the intervening segment", Virology, 298(2):317-326 (2002).
Ruiz-Arguello, et al., "Thermostability of the human respiratory syncytial virus fusion protein before and after activation: implications for the membrane-fusion mechanism", Journal of General Virology, 85:3677-3687 (2004).
Simoes et al., Respiratory syncytial virus vaccine: a systematic overview with emphasis on respiratory syncytial virus subunit vaccines. Vaccine 20:954-960 (2002).
Singh, et al., "Immunogenicity and efficacy of recombinant RSV-F vaccine in a mouse model", Vaccine, 25(33):6211-6223 (2007).
Ternette, et al., "immunogenicity and efficacy of codon optimized DNA vaccines encoding the F-protein of respiratory syncytial virus", Vaccine, 25(41):7271-7279 (2007).
Ulbrandt, et al., "Identification of antibody neutralization epitopes on the fusion protein of human metapneumovirus", Journal of General Virology, 89(Part 12)3113-3118 (2008).

* cited by examiner

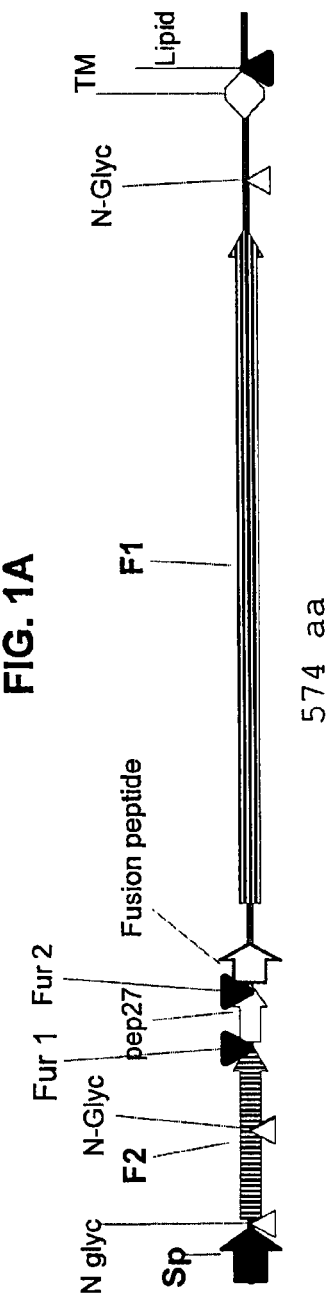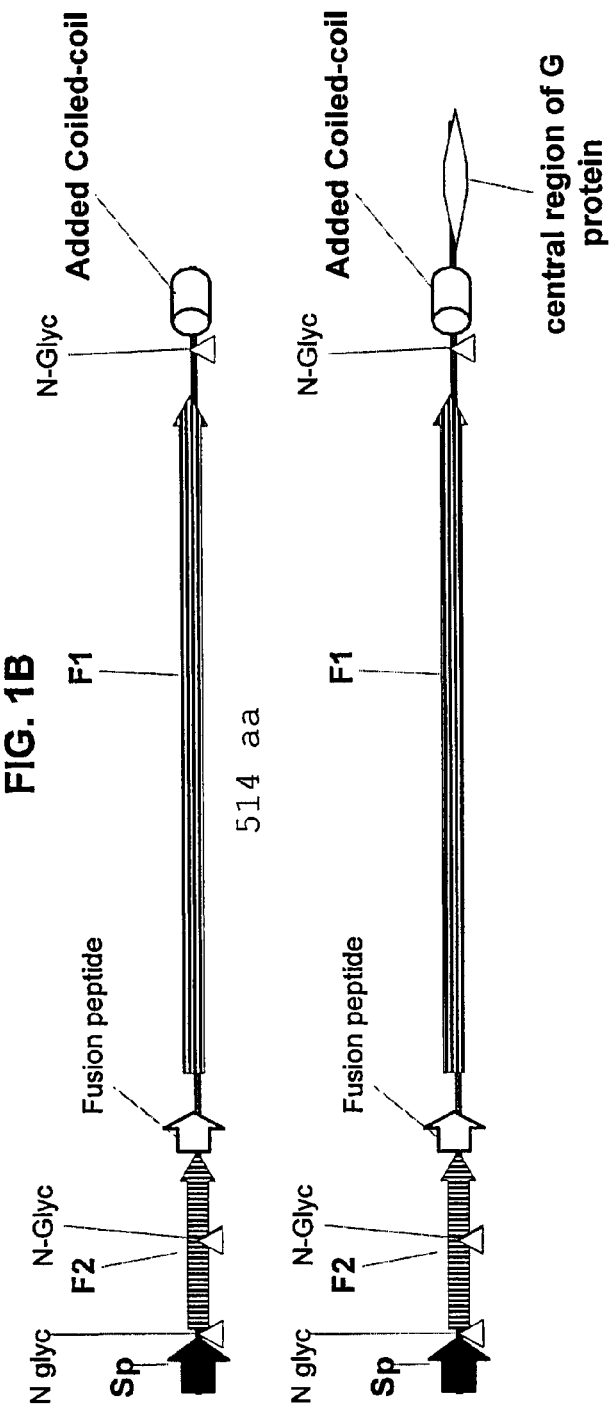
FIG. 1A
FIG. 1B

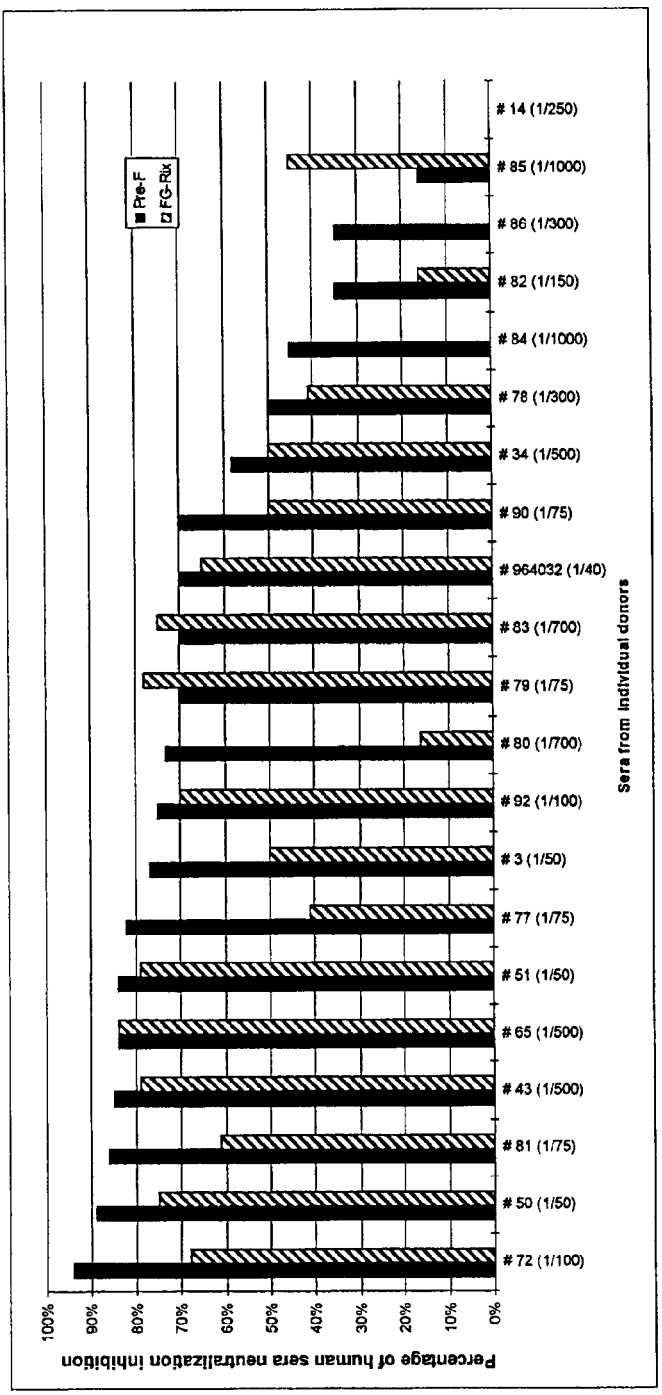

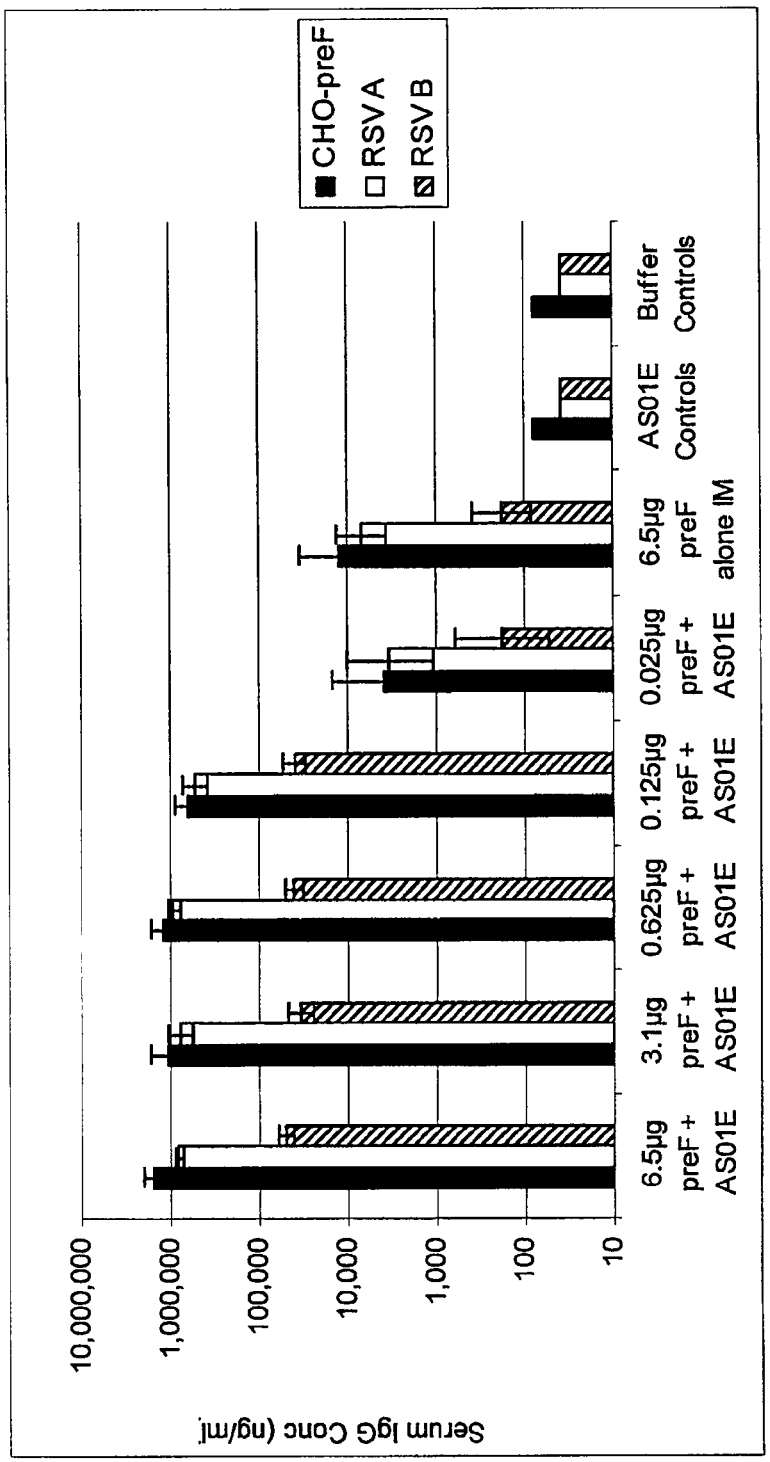

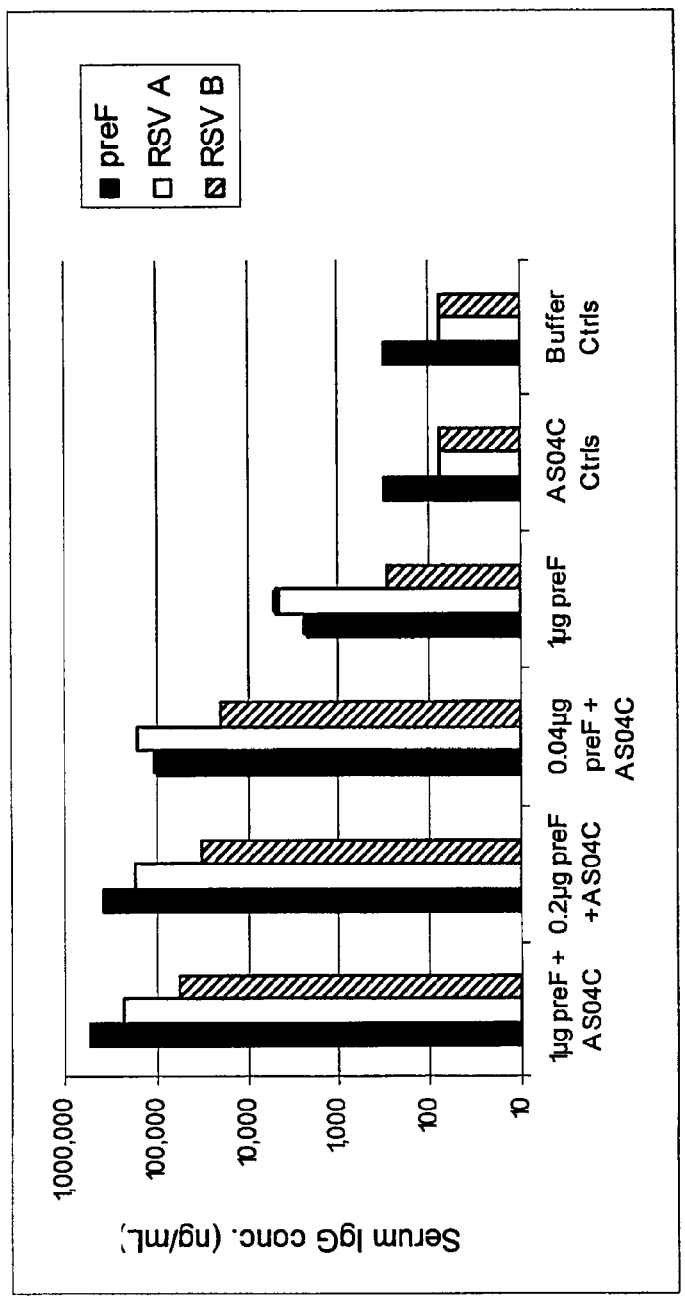

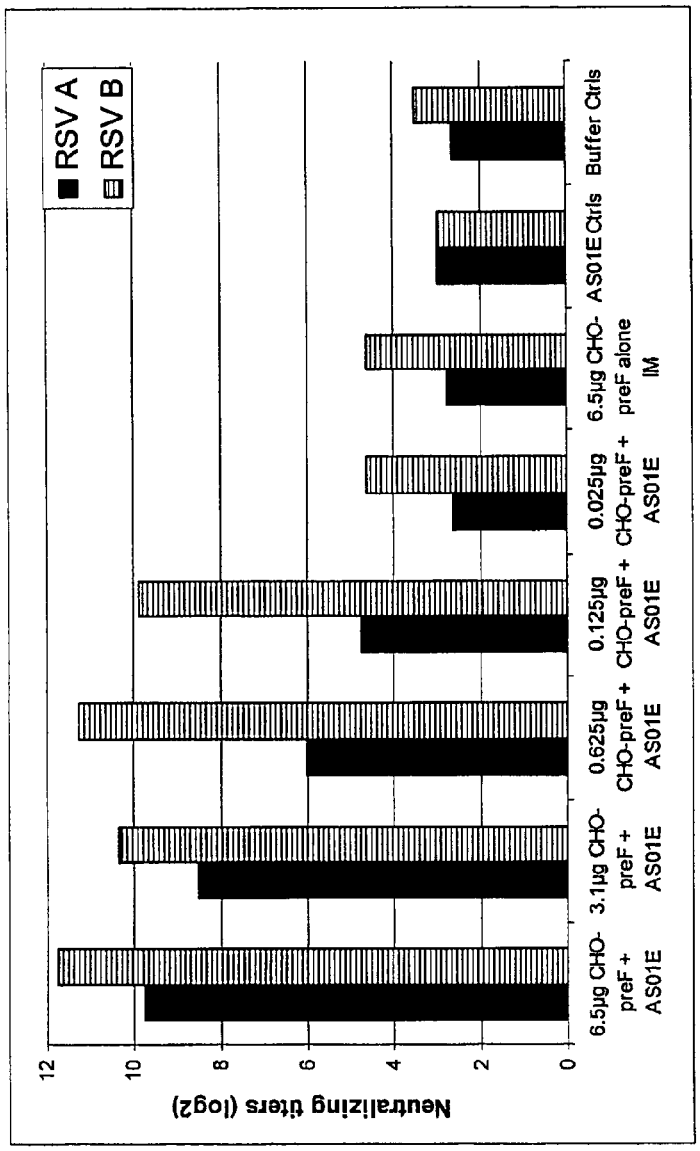

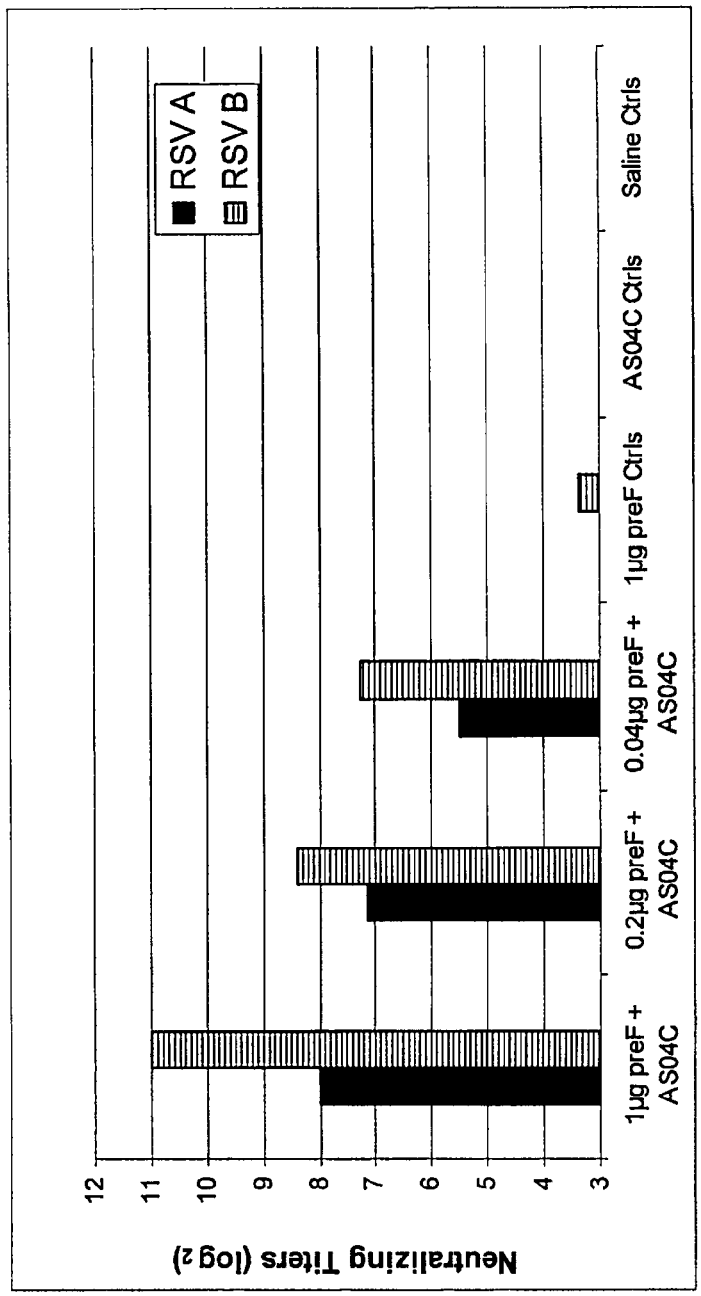

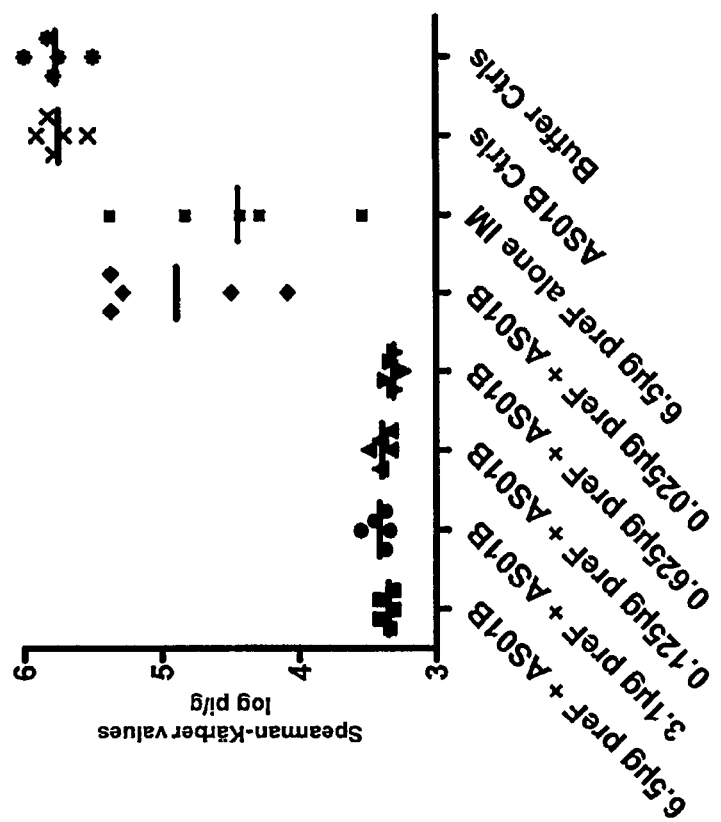

CHO-preF protection against challenge

Pulmonary eosinophil recruitment following challenge in mice

SEQUENCE LISTING

<160> NUMBER OF SEQ ID NOS: 16

<210> SEQ ID NO 1
<211> LENGTH: 1697
<212> TYPE: DNA
<213> ORGANISM: respiratory syncytial virus

<400> SEQUENCE: 1

```
atggagttgc taatcctcaa agcaaatgca attaccacaa tcctcactgc agtcacattt      60
gttttgcttc tggtcaaaac atcactgaag aattttatca atcaacatgc agtgcagtag     120
caaaggctat cttagtgctc tgagaactgg ttggtatacc agtgttataa ctatagatta     180
agtaatatca aggaaaataa gtgtaatgga acagatgcta aggtaaaatt gataaacaag     240
aattagataa atataaaaat gctgtaacag aattgcagtt gctcatgcaa agcacccagc     300
aacaaacaat cgagccagaa gagaactacc aaggtttatg aattatacac tcaaaatgcc     360
aaaaaaacca atgtaacatt aagcaagaaa aggaaaagaa gatttcttgg tttttgttag     420
gtgttggatc tgcaatcgcc agtggcgttg ctgtatctaa ggtcctgcac ctgaagggga     480
agtgaacaag atcaaaagtg ctctactatc cacaaacaag gctgtagtca gttatcaaat     540
ggagttagtg tcttaaccag caaagtgtta gacctcaaaa actatataga aaacaattgt     600
tacctattgt gaacaagcaa agctgcagca tatcaaatat agcaactgta tagagttcca     660
acaaaagaac aacagactac tagagattac cagggaattt agtgttaagc aggtgtaact     720
acacctgtaa gcacttacat gttaactaat agtgaattat tgtcattatc aatgatatgc     780
ctataacaaa tgatcagaaa aagttaatgt ccaacaatgt tcaaatgtta gacagcaaag     840
ttactctatc atgtccataa taaaagagga agtcttagca tatgtgtaca attaccacta     900
tatggtgtta tagatacacc ctgttggaaa ctacacacat ccccctatgt acaaccaaca     960
caaaagaagg gtccaacatc tgtttaacaa gaactgacag aggtggtact gtgacaatgc    1020
aggatcagta tctttcttcc cacaagctga aacatgtaaa gtcaatcaaa tcgagtattt    1080
tgtgacacaa tgaacagttt aacattacca agtgaagtaa actctgcaat gttgacatat    1140
tcaaccccaa atatgattgt aaaattatga cttcaaaaac gatgtaagca gctccgttat    1200
cacatctcta ggagccattg tgtcatgcta tggcaaaaca aatgtacagc atccaataaa    1260
aatcgtggaa tcataaagac attttctaac gggtgcgata tgtatcaaat aaaggggtgg    1320
acactgtgtc tgtaggtaac acattatatt atgtaaaaag caagaaggta aaagtctcta    1380
tgtaaaaggt gaaccaataa taaatttcta tgacccttag tattcccctc tgatgaattt    1440
gatgcatcaa tatctcaagt caacgagaag attaacagag cctagcattt attcgtaaat    1500
ccgatgaatt attacataat gtaaatgctg gtaatccacc ataaatatca tgataactac    1560
tataattata gtgattatag taatattgtt atcttaattg ctgttggact gctcttatac    1620
tgtaaggcca gaagcacacc agtcacacta agaaagatca actgagtggt ataaataata    1680
ttgcatttag taactaa                                                   1697
```

<210> SEQ ID NO 2
<211> LENGTH: 574
<212> TYPE: PRT
<213> ORGANISM: respiratory syncytial virus

<400> SEQUENCE: 2

```
Met Glu Leu Leu Ile Leu Lys Ala Asn Ala Ile Thr Thr Ile Leu Thr
1               5                   10                  15
```

```
Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
 130                 135                 140

Gly Ser Ala Ile Ala Ser Gly Val Ala Val Ser Lys Val Leu His Leu
 145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Ala Thr Val Ile Glu Phe Gln
 210                 215                 220

Gln Lys Asn Asn Arg Leu Leu Glu Ile Thr Arg Glu Phe Ser Val Asn
 225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
 290                 295                 300

Leu Tyr Gly Val Ile Asp Thr Pro Cys Trp Lys Leu His Thr Ser Pro
 305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
 370                 375                 380

Asp Ile Phe Asn Pro Lys Tyr Asp Cys Lys Ile Met Thr Ser Lys Thr
 385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
```

```
                    435                 440                 445
Thr Val Ser Val Gly Asn Thr Leu Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Ile Asn Ile Met Ile Thr
                515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 3
<211> LENGTH: 897
<212> TYPE: DNA
<213> ORGANISM: respiratory syncytial virus

<400> SEQUENCE: 3
atgtccaaaa acaaggacca acgcaccgct aagacactag aaaagacctg ggacactctc      60
aatcatttat tattcatatc atcgggctta tataagttaa atcttaaatc tatagcacaa     120
atcacattat ccattctggc aatgataatc tcaacttcac ttataattac agccatcata     180
ttcatagcct cggcaaacca caagtcaca ctaacaactg caatcataca agatgcaaca     240
agccagatca gaacacaac cccaacatac ctcactcagg atcctcagct tggaatcagc     300
ttctccaatc tgtctgaaat tacatcacaa accaccacca tactagcttc aacaacacca     360
ggagtcaagt caaacctgca acccacaaca gtcaagacta aaacacaac aaaacccaa     420 acacaaccca gcaagcccac tacaaaacaa cgccaaaaca accaccaaa caaacccaat     480 aatgattttc acttcgaagt gtttaacttt gtaccctgca gcatatgcag caacaatcca     540
acctgctggg ctatctgcaa aagaatacca acaaaaaac caggaaagaa accaccacc     600 aagcctacaa aaaaaccaac cttcaagaca accaaaaaag atctcaaacc tcaaaccact     660
aaaccaaagg aagtacccac caccaagccc acagaagagc caaccatcaa cccaccaaa     720 acaaacatca caactacact gctcaccaac aacaccacag aaatccaaa actcacaagt     780 caaatggaaa ccttccactc aacctcctcc gaaggcaatc taagcccttc tcaagtctcc     840
acaacatccg agcacccatc acaaccctca tctccaccca acacaacacg ccagtag      897

<210> SEQ ID NO 4
<211> LENGTH: 298
<212> TYPE: PRT
<213> ORGANISM: respiratory syncytial virus

<400> SEQUENCE: 4

Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45
```

-continued

```
Ile Ile Ser Thr Ser Leu Ile Ile Thr Ala Ile Ile Phe Ile Ala Ser
            50                  55                  60

Ala Asn His Lys Val Thr Leu Thr Thr Ala Ile Ile Gln Asp Ala Thr
 65                  70                  75                  80

Ser Gln Ile Lys Asn Thr Thr Pro Thr Tyr Leu Thr Gln Asp Pro Gln
                 85                  90                  95

Leu Gly Ile Ser Phe Ser Asn Leu Ser Glu Ile Thr Ser Gln Thr Thr
                100                 105                 110

Thr Ile Leu Ala Ser Thr Thr Pro Gly Val Lys Ser Asn Leu Gln Pro
            115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp Leu Lys Pro Gln Thr Thr Lys Pro Lys Glu
210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295
```

<210> SEQ ID NO 5
<211> LENGTH: 1566
<212> TYPE: DNA
<213> ORGANISM: Artificial Sequence
<220> FEATURE:
<223> OTHER INFORMATION: Recombinant PreF polynucleotide

<400> SEQUENCE: 5

```
aagcttgcca ccatggagct gctgatcctg aaaaccaacg ccatcaccgc catcctggcc      60
gccgtgaccc tgtgcttcgc ctcctcccag aacatcaccg aggagttcta ccagtccacc     120
tgctccgccg tgtccaaggg ctacctgtcc gccctgcgga ccggctggta cacctccgtg     180
atcaccatcg agctgtccaa catcaaggaa aacaagtgca acggcaccga cgccaaggtg     240
aagctgatca gcaggagct ggacaagtac aagagcgccg tgaccgaact ccagctgctg     300
atgcagtcca cccctgccac caacaacaag tttctgggct tcctgctggg cgtgggctcc     360
gccatcgcct ccggcatcgc cgtgagcaag gtgctgcacc tggagggcga ggtgaacaag     420
atcaagagcg ccctgctgtc caccaacaag gccgtggtgt ccctgtccaa cggcgtgtcc     480
gtgctgacct ccaaggtgct ggatctgaag aactacatcg acaagcagct gctgcctatc     540
gtgaacaagc agtcctgctc catctccaac atcgagaccg tgatcgagtt ccagcagaag     600
aacaaccggc tgctggagat cacccgcgag ttctccgtga acgccggcgt gaccacccct     660
```

```
gtgtccacct acatgctgac caactccgag ctgctgtccc tgatcaacga catgcctatc    720
accaacgacc agaaaaaact gatgtccaac aacgtgcaga tcgtgcggca gcagtcctac    780
agcatcatga gcatcatcaa ggaagaggtg ctggcctacg tggtgcagct gcctctgtac    840
ggcgtgatcg acaccccttg ctggaagctg cacacctccc ccctgtgcac caccaacacc    900
aaggagggct ccaacatctg cctgacccgg accgaccggg gctggtactg cgacaacgcc    960
ggctccgtgt ccttcttccc tctggccgag acctgcaagg tgcagtccaa ccgggtgttc   1020
tgcgacacca tgaactccct gaccctgcct ccgaggtga acctgtgcaa catcgacatc   1080 ttcaaccca gtacgactg caagatcatg accagcaaga ccgacgtgtc ctccagcgtg   1140
atcacctccc tgggcgccat cgtgtcctgc tacggcaaga ccaagtgcac cgcctccaac   1200
aagaaccggg gaatcatcaa gaccttctcc aacggctgcg actacgtgtc caataagggc   1260
gtggacaccg tgtccgtggg caacacactg tactacgtga ataagcagga gggcaagagc   1320
ctgtacgtga agggcgagcc tatcatcaac ttctacgacc ctctggtgtt cccttccgac   1380
gagttcgacg cctccatcag ccaggtgaac gagaagatca accagtccct ggccttcatc   1440
cggaagtccg acgagaagct gcataacgtg gaggacaaga tcgaggagat cctgtccaaa   1500
atctaccaca tcgagaacga gatcgcccgg atcaagaagc tgatcggcga ggcctgataa   1560
tctaga                                                              1566
```

<210> SEQ ID NO 6
<211> LENGTH: 514
<212> TYPE: PRT
<213> ORGANISM: Artificial Sequence
<220> FEATURE:
<223> OTHER INFORMATION: Recombinant PreF Antigen

<400> SEQUENCE: 6

```
Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Leu
            100                 105                 110

Gly Val Gly Ser Ala Ile Ala Ser Gly Ile Ala Val Ser Lys Val Leu
        115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
```

Val Asn Ala Gly Val Thr Thr Pro Val Ser Thr Tyr Met Leu Thr Asn
195                 200                 205                 210

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
            245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
            275                 280                 285

Ser Pro Leu Cys Thr Thr Asn Thr Lys Glu Gly Ser Asn Ile Cys Leu
290                 295                 300

Thr Arg Thr Asp Arg Gly Trp Tyr Cys Asp Asn Ala Gly Ser Val Ser
305                 310                 315                 320

Phe Phe Pro Leu Ala Glu Thr Cys Lys Val Gln Ser Asn Arg Val Phe
            325                 330                 335

Cys Asp Thr Met Asn Ser Leu Thr Leu Pro Ser Glu Val Asn Leu Cys
            340                 345                 350

Asn Ile Asp Ile Phe Asn Pro Lys Tyr Asp Cys Lys Ile Met Thr Ser
            355                 360                 365

Lys Thr Asp Val Ser Ser Ser Val Ile Thr Ser Leu Gly Ala Ile Val
370                 375                 380

Ser Cys Tyr Gly Lys Thr Lys Cys Thr Ala Ser Asn Lys Asn Arg Gly
385                 390                 395                 400

Ile Ile Lys Thr Phe Ser Asn Gly Cys Asp Tyr Val Ser Asn Lys Gly
            405                 410                 415

Val Asp Thr Val Ser Val Gly Asn Thr Leu Tyr Tyr Val Asn Lys Gln
            420                 425                 430

Glu Gly Lys Ser Leu Tyr Val Lys Gly Glu Pro Ile Ile Asn Phe Tyr
            435                 440                 445

Asp Pro Leu Val Phe Pro Ser Asp Glu Phe Asp Ala Ser Ile Ser Gln
450                 455                 460

Val Asn Glu Lys Ile Asn Gln Ser Leu Ala Phe Ile Arg Lys Ser Asp
465                 470                 475                 480

Glu Lys Leu His Asn Val Glu Asp Lys Ile Glu Ile Leu Ser Lys
            485                 490                 495

Ile Tyr His Ile Glu Asn Glu Ile Ala Arg Ile Lys Lys Leu Ile Gly
            500                 505                 510

Glu Ala

<210> SEQ ID NO 7
<211> LENGTH: 1855
<212> TYPE: DNA
<213> ORGANISM: Artificial Sequence
<220> FEATURE:
<223> OTHER INFORMATION: Chimeric PreF-G Antigen polynucleotide seqeunce

<400> SEQUENCE: 7
aagcttgcca ccatggagct gctgatcctc aagaccaacg ccatcaccgc catcctggcc    60
gccgtgaccc tgtgcttcgc ctcctcccag aacatcacca agagttcta ccagtccacc   120 tgctccgccg tgtccaaggg ctacctgtcc gccctgcgga ccggctggta cacctccgtg   180
atcaccatcg agctgtccaa catcaaagaa acaagtgca acggcaccga cgccaaggtc   240
aagctgatca agcaggaact ggacaagtac aagagcgccg tgaccgaact ccagctgctg   300

```
atgcagtcca ccoctgccac caacaacaag aagtttctgg gcttcctgct gggcgtgggc    360
tccgccatcg cctccggcat cgccgtgagc aaggtgctgc cctggaggg cgaggtgaac    420 aagatcaaga gcgccctgct gtccaccaac aaggccgtgg tgtccctgtc aacggcgtg    480 tccgtgctga cctccaaggt gctggatctg aagaactaca tcgacaagca gctgctgcct    540
atcgtgaaca gcagtcctg ctccatctcc aacatcgaga ccgtgatcga gttccagcag    600
aagaacaacc ggctgctgga gatcacccgc gagttctccg tgaacgccgg cgtgaccacc    660
cctgtgtcca cctacatgct gacaaactcc gagctgctct ccctgatcaa cgacatgcct    720
atcaccaacg accaaaaaaa gctgatgtcc aacaacgtgc agatcgtgcg gcagcagtcc    780
tacagcatca tgagcatcat caaggaagaa gtcctggcct acgtcgtgca gctgcctctg    840
tacggcgtga tcgacacccc ttgctggaag ctgcacacct cccccctgtg caccaccaac    900
accaaagagg ctccaacat ctgcctgacc cggaccgacc ggggctggta ctgcgacaac    960
gccggctccg tgtccttctt ccctctggcc gagacctgca aggtgcagtc caaccgggtg    1020
ttctgcgaca ccatgaactc cctgaccctg ccttccgagg tgaacctgtg caacatcgac    1080
atcttcaacc ccaagtacga ctgcaagatc atgaccagca gaccgacgt gtcctccagc    1140 gtgatcacct ccctgggcgc catcgtgtcc tgctacggca agaccaagtg caccgcctcc    1200
aacaagaacc gggaatcat caagaccttc tccaacggct gcgactacgt gtccaataag    1260
ggcgtggaca ccgtgtccgt gggcaacaca ctgtactacg tgaataagca ggaaggcaag    1320
agcctgtacg tgaagggcga gcctatcatc aacttctacg accctctggt gttcccttcc    1380
gacgagttcg acgcctccat cagccaggtc aacgagaaga tcaaccagtc cctggccttc    1440
atccggaagt ccgacgagaa gctgcataac gtggaggaca agatcgaaga gatcctgtcc    1500
aaaatctacc acatcgagaa cgagatcgcc cggatcaaga gctgatcgg cgaggctggc    1560 ggctctggcg gcagcggcgg ctccaagcag cggcagaaca agcctcctaa caagcccaac    1620
aacgacttcc acttcgaggt gttcaacttc gtgccttgct ccatctgctc caacaaccct    1680
acctgctggg ccatctgcaa gagaatcccc aacaagaagc ctggcaagaa accaccacc    1740 aagcctacca agaagcctac cttcaagacc accaagaagg accacaagcc tcagaccaca    1800
aagcctaagg aagtgccaac caccaagcac caccaccatc accactgata atcta    1855
```

<210> SEQ ID NO 8
<211> LENGTH: 605
<212> TYPE: PRT
<213> ORGANISM: Artificial Sequence
<220> FEATURE:
<223> OTHER INFORMATION: Chimeric PreF-G polypeptide

<400> SEQUENCE: 8

```
Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95
```

```
Met Gln Ser Thr Pro Ala Thr Asn Asn Lys Lys Phe Leu Gly Phe Leu
            100                 105                 110

Leu Gly Val Gly Ser Ala Ile Ala Ser Gly Ile Ala Val Ser Lys Val
            115                 120                 125

Leu His Leu Glu Gly Glu Val Asn Lys Ile Lys Ser Ala Leu Leu Ser
        130                 135                 140

Thr Asn Lys Ala Val Val Ser Leu Ser Asn Gly Val Ser Val Leu Thr
145                 150                 155                 160

Ser Lys Val Leu Asp Leu Lys Asn Tyr Ile Asp Lys Gln Leu Leu Pro
                165                 170                 175

Ile Val Asn Lys Gln Ser Cys Ser Ile Ser Asn Ile Glu Thr Val Ile
            180                 185                 190

Glu Phe Gln Gln Lys Asn Asn Arg Leu Leu Glu Ile Thr Arg Glu Phe
            195                 200                 205

Ser Val Asn Ala Gly Val Thr Thr Pro Val Ser Thr Tyr Met Leu Thr
        210                 215                 220

Asn Ser Glu Leu Leu Ser Leu Ile Asn Asp Met Pro Ile Thr Asn Asp
225                 230                 235                 240

Gln Lys Lys Leu Met Ser Asn Asn Val Gln Ile Val Arg Gln Gln Ser
                245                 250                 255

Tyr Ser Ile Met Ser Ile Ile Lys Glu Glu Val Leu Ala Tyr Val Val
            260                 265                 270

Gln Leu Pro Leu Tyr Gly Val Ile Asp Thr Pro Cys Trp Lys Leu His
        275                 280                 285

Thr Ser Pro Leu Cys Thr Thr Asn Thr Lys Glu Gly Ser Asn Ile Cys
        290                 295                 300

Leu Thr Arg Thr Asp Arg Gly Trp Tyr Cys Asp Asn Ala Gly Ser Val
305                 310                 315                 320

Ser Phe Phe Pro Leu Ala Glu Thr Cys Lys Val Gln Ser Asn Arg Val
                325                 330                 335

Phe Cys Asp Thr Met Asn Ser Leu Thr Leu Pro Ser Glu Val Asn Leu
            340                 345                 350

Cys Asn Ile Asp Ile Phe Asn Pro Lys Tyr Asp Cys Lys Ile Met Thr
        355                 360                 365

Ser Lys Thr Asp Val Ser Ser Ser Val Ile Thr Ser Leu Gly Ala Ile
        370                 375                 380

Val Ser Cys Tyr Gly Lys Thr Lys Cys Thr Ala Ser Asn Lys Asn Arg
385                 390                 395                 400

Gly Ile Ile Lys Thr Phe Ser Asn Gly Cys Asp Tyr Val Ser Asn Lys
                405                 410                 415

Gly Val Asp Thr Val Ser Val Gly Asn Thr Leu Tyr Tyr Val Asn Lys
            420                 425                 430

Gln Glu Gly Lys Ser Leu Tyr Val Lys Gly Glu Pro Ile Ile Asn Phe
        435                 440                 445

Tyr Asp Pro Leu Val Phe Pro Ser Asp Glu Phe Asp Ala Ser Ile Ser
450                 455                 460

Gln Val Asn Glu Lys Ile Asn Gln Ser Leu Ala Phe Ile Arg Lys Ser
465                 470                 475                 480

Asp Glu Lys Leu His Asn Val Glu Asp Lys Ile Glu Glu Ile Leu Ser
                485                 490                 495

Lys Ile Tyr His Ile Glu Asn Glu Ile Ala Arg Ile Lys Lys Leu Ile
            500                 505                 510

Gly Glu Ala Gly Gly Ser Gly Gly Ser Gly Gly Ser Lys Gln Arg Gln
```

|  |  |  | 515 |  |  |  | 520 |  |  |  | 525 |  |
| --- | --- | --- | --- | --- | --- | --- | --- | --- | --- | --- | --- | --- |

Asn Lys Pro Pro Asn Lys Pro Asn Asn Asp Phe His Phe Glu Val Phe
    530                        535                   540

Asn Phe Val Pro Cys Ser Ile Cys Ser Asn Asn Pro Thr Cys Trp Ala
545                       550                   555                   560

Ile Cys Lys Arg Ile Pro Asn Lys Lys Pro Gly Lys Lys Thr Thr Thr
            565                   570                   575

Lys Pro Thr Lys Lys Pro Thr Phe Lys Thr Thr Lys Lys Asp His Lys
            580                   585                   590

Pro Gln Thr Thr Lys Pro Lys Glu Val Pro Thr Thr Lys
            595                   600                   605

<210> SEQ ID NO 9
<211> LENGTH: 1834
<212> TYPE: DNA
<213> ORGANISM: Artificial Sequence
<220> FEATURE:
<223> OTHER INFORMATION: Chimeric PreF-G polynucleotide

<400> SEQUENCE: 9

```
aagcttgcca ccatggagct gctgatcctc aagaccaacg ccatcaccgc catcctggcc    60
gccgtgaccc tgtgcttcgc ctcctcccag aacatcaccg aagagttcta ccagtccacc   120
tgctccgccg tgtccaaggg ctacctgtcc gccctgcgga ccggctggta cacctccgtg   180
atcaccatcg agctgtccaa catcaaagaa aacaagtgca acggcaccga cgccaaggtc   240
aagctgatca gcaggaact ggacaagtac aagagcgccg tgaccgaact ccagctgctg   300
atgcagtcca cccctgccac caacaacaag aagtttctgg gcttcctgct gggcgtgggc   360
tccgccatcg cctccggcat cgccgtgagc aaggtgctgc acctggaggg cgaggtgaac   420
aagatcaaga gcgccctgct gtccaccaac aaggccgtgg tgtccctgtc caacggcgtg   480
tccgtgctga cctccaaggt gctggatctg aagaactaca tcgacaagca gctgctgcct   540
atcgtgaaca agcagtcctg ctccatctcc aacatcgaga ccgtgatcga gttccagcag   600
aagaacaacc ggctgctgga gatcacccgc gagttctccg tgaacgccgg cgtgaccacc   660
cctgtgtcca cctacatgct gacaaactcc gagctgctct ccctgatcaa cgacatgcct   720
atcaccaacg accaaaaaaa gctgatgtcc aacaacgtgc agatcgtgcg gcagcagtcc   780
tacagcatca tgagcatcat caaggaagaa gtcctggcct acgtcgtgca gctgcctctg   840
tacggcgtga tcgacacccc ttgctggaag ctgcacacct cccccctgtg caccaccaac   900
accaaagagg gctccaacat ctgcctgacc cggaccgacc ggggctggta ctgcgacaac   960
gccggctccg tgtccttctt ccctctggcc gagacctgca aggtgcagtc caaccgggtg  1020
ttctgcgaca ccatgaactc cctgaccctg ccttccgagg tgaacctgtg caacatcgac  1080
atcttcaacc ccaagtacga ctgcaagatc atgaccagca gaccgacgt gtcctccagc  1140
gtgatcacct ccctgggcgc catcgtgtcc tgctacggca gaccaagtg caccgcctcc  1200
aacaagaacc gggaatcat caagaccttc tccaacggct gcgactacgt gtccaataag  1260
ggcgtggaca ccgtgtccgt gggcaacaca ctgtactacg tgaataagca ggaaggcaag  1320
agcctgtacg tgaagggcga gcctatcatc aacttctacg accctctggt gttcccttcc  1380
gacgagttcg acgcctccat cagccaggtc aacgagaaga tcaaccagtc cctggccttc  1440
atccggaagt ccgacgagaa gctgcataac gtggaggaca agatcgaaga gatcctgtcc  1500
aaaatctacc acatcgagaa cgagatcgcc cggatcaaga agctgatcgg cgaggctggc  1560
ggcaagcagc ggcagaacaa gcctcctaac aagcccaaca cgacttcca cttcgaggtg  1620
```

-continued

```
ttcaacttcg tgccttgctc catctgctcc aacaaccccta cctgctgggc catctgcaag    1680
agaatcccca acaagaagcc tggcaagaaa accaccacca agcctaccaa gaagcctacc    1740
ttcaagacca ccaagaagga ccacaagcct cagaccacaa agcctaagga agtgccaacc    1800
accaagcacc accaccatca ccactgataa tcta                                 1834
```

<210> SEQ ID NO 10
<211> LENGTH: 598
<212> TYPE: PRT
<213> ORGANISM: Artificial Sequence
<220> FEATURE:
<223> OTHER INFORMATION: Chimeric PreF-G polypeptide

<400> SEQUENCE: 10

```
Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Lys Phe Leu Gly Phe Leu
            100                 105                 110

Leu Gly Val Gly Ser Ala Ile Ala Ser Gly Ile Ala Val Ser Lys Val
        115                 120                 125

Leu His Leu Glu Gly Glu Val Asn Lys Ile Lys Ser Ala Leu Leu Ser
    130                 135                 140

Thr Asn Lys Ala Val Val Ser Leu Ser Asn Gly Val Ser Val Leu Thr
145                 150                 155                 160

Ser Lys Val Leu Asp Leu Lys Asn Tyr Ile Asp Lys Gln Leu Leu Pro
                165                 170                 175

Ile Val Asn Lys Gln Ser Cys Ser Ile Ser Asn Ile Glu Thr Val Ile
            180                 185                 190

Glu Phe Gln Gln Lys Asn Asn Arg Leu Leu Glu Ile Thr Arg Glu Phe
        195                 200                 205

Ser Val Asn Ala Gly Val Thr Thr Pro Val Ser Thr Tyr Met Leu Thr
    210                 215                 220

Asn Ser Glu Leu Leu Ser Leu Ile Asn Asp Met Pro Ile Thr Asn Asp
225                 230                 235                 240

Gln Lys Lys Leu Met Ser Asn Asn Val Gln Ile Val Arg Gln Gln Ser
                245                 250                 255

Tyr Ser Ile Met Ser Ile Ile Lys Glu Glu Val Leu Ala Tyr Val Val
            260                 265                 270

Gln Leu Pro Leu Tyr Gly Val Ile Asp Thr Pro Cys Trp Lys Leu His
        275                 280                 285

Thr Ser Pro Leu Cys Thr Thr Asn Thr Lys Glu Gly Ser Asn Ile Cys
    290                 295                 300

Leu Thr Arg Thr Asp Arg Gly Trp Tyr Cys Asp Asn Ala Gly Ser Val
305                 310                 315                 320

Ser Phe Phe Pro Leu Ala Glu Thr Cys Lys Val Gln Ser Asn Arg Val
```

```
                           325                 330                 335
Phe Cys Asp Thr Met Asn Ser Leu Thr Leu Pro Ser Glu Val Asn Leu
                340                 345                 350

Cys Asn Ile Asp Ile Phe Asn Pro Lys Tyr Asp Cys Lys Ile Met Thr
            355                 360                 365

Ser Lys Thr Asp Val Ser Ser Val Ile Thr Ser Leu Gly Ala Ile
    370                 375                 380

Val Ser Cys Tyr Gly Lys Thr Lys Cys Thr Ala Ser Asn Lys Asn Arg
385                 390                 395                 400

Gly Ile Ile Lys Thr Phe Ser Asn Gly Cys Asp Tyr Val Ser Asn Lys
                405                 410                 415

Gly Val Asp Thr Val Ser Val Gly Asn Thr Leu Tyr Tyr Val Asn Lys
            420                 425                 430

Gln Glu Gly Lys Ser Leu Tyr Val Lys Gly Glu Pro Ile Ile Asn Phe
        435                 440                 445

Tyr Asp Pro Leu Val Phe Pro Ser Asp Glu Phe Asp Ala Ser Ile Ser
    450                 455                 460

Gln Val Asn Glu Lys Ile Asn Gln Ser Leu Ala Phe Ile Arg Lys Ser
465                 470                 475                 480

Asp Glu Lys Leu His Asn Val Glu Asp Lys Ile Glu Ile Leu Ser
                485                 490                 495

Lys Ile Tyr His Ile Glu Asn Glu Ile Ala Arg Ile Lys Lys Leu Ile
            500                 505                 510

Gly Glu Ala Gly Gly Lys Gln Arg Gln Asn Lys Pro Pro Asn Lys Pro
        515                 520                 525

Asn Asn Asp Phe His Phe Glu Val Phe Asn Phe Val Pro Cys Ser Ile
    530                 535                 540

Cys Ser Asn Asn Pro Thr Cys Trp Ala Ile Cys Lys Arg Ile Pro Asn
545                 550                 555                 560

Lys Lys Pro Gly Lys Lys Thr Thr Thr Lys Pro Thr Lys Lys Pro Thr
                565                 570                 575

Phe Lys Thr Thr Lys Lys Asp His Lys Pro Gln Thr Thr Lys Pro Lys
            580                 585                 590

Glu Val Pro Thr Thr Lys
        595

<210> SEQ ID NO 11
<211> LENGTH: 28
<212> TYPE: PRT
<213> ORGANISM: Artificial Sequence
<220> FEATURE:
<223> OTHER INFORMATION: Isoleucine substituted GCN4 leucine zipper

<400> SEQUENCE: 11

Glu Asp Lys Ile Glu Glu Ile Leu Ser Lys Ile Tyr His Ile Glu Asn
1               5                   10                  15

Glu Ile Ala Arg Ile Lys Lys Leu Ile Gly Glu Ala
            20                  25

<210> SEQ ID NO 12
<211> LENGTH: 1563
<212> TYPE: DNA
<213> ORGANISM: Artificial sequence
<220> FEATURE:
<223> OTHER INFORMATION: Codon optimized PreF nucleotide sequence

<400> SEQUENCE: 12
atggagctgc ccatcctgaa gaccaacgcc atcaccacca tcctcgccgc cgtgaccctg      60
```

```
tgcttcgcca gcagccagaa catcacggag gagttctacc agagcacgtg cagcgccgtg    120
agcaagggct acctgagcgc gctgcgcacg ggctggtaca cgagcgtgat cacgatcgag    180
ctgagcaaca tcaaggagaa caagtgcaac ggcacggacg cgaaggtgaa gctgatcaag    240
caggagctgg acaagtacaa gagcgcggtg acggagctgc agctgctgat gcagagcacg    300
ccggcgacga caacaagtt cctcggcttc ctgctgggcg tgggcagcgc gatcgcgagc    360
ggcatcgccg tgagcaaggt gctgcacctg gagggcgagg tgaacaagat caagtccgcg    420
ctgctgagca cgaacaaggc ggtcgtgagc ctgagcaacg cgtgagcgt gctgacgagc    480 aaggtgctcg acctgaagaa ctacatcgac aagcagctgc tgccgatcgt gaacaagcag    540
agctgcagca tcagcaacat cgagaccgtg atcgagttcc agcagaagaa caaccgcctg    600
ctggagatca cgcgggagtt ctccgtgaac gcaggcgtga cgacgcccgt gtctacgtac    660
atgctgacga cagcgagct gctcagcctg atcaacgaca tgccgatcac gaacgaccag    720
aagaagctga tgagcaacaa cgtgcagatc gtgcgccagc agagctacag catcatgagc    780
atcatcaagg aggaggtgct ggcatacgtg gtgcagctgc cgctgtacgg cgtcatcgac    840 acgcccctgct ggaagctgca cacgagcccg ctgtgcacga ccaacacgaa ggagggcagc    900
aacatctgcc tgacgcggac ggaccggggc tggtactgcg acaacgcggg cagcgtgagc    960
ttcttcccgc tcgcggagac gtgcaaggtg cagagcaacc gcgtcttctg cgacacgatg    1020
aacagcctga cgctgccgag cgaggtgaac ctgtgcaaca tcgacatctt caaccccgaag    1080 tacgactgca agatcatgac gagcaagacc gatgtcagca gcagcgtgat cacgagcctc    1140
ggcgcgatcg tgagctgcta cggcaagacg aagtgcacgg cgagcaacaa gaaccgcggc    1200
atcatcaaga cgttcagcaa cggctgcgac tatgtgagca caagggcgt ggacactgtg    1260 agcgtcggca cacgctgta ctacgtgaac aagcaggagg gcaagagcct gtacgtgaag    1320
ggcgagccga tcatcaactt ctacgacccg ctcgtgttcc cgagcgacga gttcgacgcg    1380
agcatcagcc aagtgaacga gaagatcaac cagagcctgg cgttcatccg caagagcgac    1440
gagaagctgc acaacgtgga ggacaagatc gaggagatcc tgagcaagat ctaccacatc    1500
gagaacgaga tcgcgcgcat caagaagctg atcggcgagg cgcatcatca ccatcaccat    1560
tga                                                                 1563
```

<210> SEQ ID NO 13
<211> LENGTH: 1685
<212> TYPE: DNA
<213> ORGANISM: Artificial sequence
<220> FEATURE:
<223> OTHER INFORMATION: PreF polynucleotide sequence with intron

<400> SEQUENCE: 13

```
atggagctgc tgatcctgaa aaccaacgcc atcaccgcca tcctggccgc cgtgaccctg     60
tgcttcgcct cctcccagaa catcaccgag gagttctacc agtccacctg ctccgccgtg    120
tccaagggct acctgtccgc cctgcggacc ggctggtaca cctccgtgat caccatcgag    180
ctgtccaaca tcaaggaaaa caagtgcaac ggcaccgacg ccaaggtgaa gctgatcaag    240
caggagctgg acaagtacaa gagcgccgtg accgaactcc agctgctgat gcagtccacc    300
cctgccacca caacaagtt tctgggcttc ctgctgggcg tgggctccgc catcgcctcc    360
ggcatcgccg tgagcaaggt acgtgtcggg acttgtgttc ccctttttt aataaaaagt    420 tatatcttta atgttatata catatttcct gtatgtgatc catgtgctta tgactttgtt    480
tatcatgtgt ttaggtgctg cacctggagg gcgaggtgaa caagatcaag agcgccctgc    540
```

```
tgtccaccaa caaggccgtg gtgtccctgt ccaacggcgt gtccgtgctg acctccaagg    600
tgctggatct gaagaactac atcgacaagc agctgctgcc tatcgtgaac aagcagtcct    660
gctccatctc caacatcgag accgtgatcg agttccagca gaagaacaac cggctgctgg    720
agatcacccg cgagttctcc gtgaacgccg gcgtgaccac ccctgtgtcc acctacatgc    780
tgaccaactc cgagctgctg tccctgatca cgacatgcc tatcaccaac gaccagaaaa    840
aactgatgtc caacaacgtg cagatcgtgc ggcagcagtc ctacagcatc atgagcatca    900
tcaaggaaga ggtgctggcc tacgtggtgc agctgcctct gtacggcgtg atcgacaccc    960
cttgctggaa gctgcacacc tcccccctgt gcaccaccaa caccaaggag ggctccaaca   1020
tctgcctgac ccggaccgac cggggctggt actgcgacaa cgccggctcc gtgtccttct   1080
tccctctggc cgagacctgc aaggtgcagt ccaaccgggt gttctgcgac accatgaact   1140
ccctgaccct gccttccgag gtgaacctgt gcaacatcga catcttcaac cccaagtacg   1200
actgcaagat catgaccagc aagaccgacg tgtcctccag cgtgatcacc tccctgggcg   1260
ccatcgtgtc ctgctacggc aagaccaagt gcaccgcctc caacaagaac cggggaatca   1320
tcaagacctt ctccaacggc tgcgactacg tgtccaataa gggcgtggac accgtgtccg   1380
tgggcaacac actgtactac gtgaataagc aggagggcaa gagcctgtac gtgaagggcg   1440
agcctatcat caacttctac gaccctctgg tgttccccttc cgacgagttc gacgcctcca   1500
tcagccaggt gaacgagaag atcaaccagt ccctggcctt catccggaag tccgacgaga   1560
agctgcataa cgtggaggac aagatcgagg agatcctgtc caaaatctac cacatcgaga   1620
acgagatcgc ccggatcaag aagctgatcg gcgaggccgg aggtcaccac caccatcacc   1680
actga                                                              1685
```

<210> SEQ ID NO 14
<211> LENGTH: 9
<212> TYPE: PRT
<213> ORGANISM: Artificial sequence
<220> FEATURE:
<223> OTHER INFORMATION: Synthetic linker peptide

<400> SEQUENCE: 14

Gly Gly Ser Gly Gly Ser Gly Gly Ser
1               5

<210> SEQ ID NO 15
<211> LENGTH: 4
<212> TYPE: PRT
<213> ORGANISM: Artificial sequence
<220> FEATURE:
<223> OTHER INFORMATION: Furin cleavage consensus motif

<400> SEQUENCE: 15

Arg Ala Arg Arg
1

<210> SEQ ID NO 16
<211> LENGTH: 4
<212> TYPE: PRT
<213> ORGANISM: Artificial sequence
<220> FEATURE:
<223> OTHER INFORMATION: Furin cleavage consensus motif

<400> SEQUENCE: 16

Arg Lys Arg Arg
1

RECOMBINANT RSV ANTIGENS

CROSS-REFERENCE TO RELATED APPLICATION

This application is the US National Stage under §371 of International Application No. PCT/CA2008/002277, filed 23 Dec. 2008, which claims benefit of the filing date of U.S. Provisional Applications No. 61/056,206, filed 27 May 2008, and No. 61/016,524, filed 24 Dec. 2007, all of which are incorporated herein by reference.

COPYRIGHT NOTIFICATION PURSUANT TO 37 C.F.R. §1.71(E)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

This disclosure concerns the field of immunology. More particularly this disclosure relates to compositions and methods for eliciting an immune response specific for Respiratory Syncytial Virus (RSV).

Human Respiratory Syncytial Virus (RSV) is the most common worldwide cause of lower respiratory tract infections (LRI) in infants less than 6 months of age and premature babies less than or equal to 35 weeks of gestation. The RSV disease spectrum includes a wide array of respiratory symptoms from rhinitis and otitis to pneumonia and bronchiolitis, the latter two diseases being associated with considerable morbidity and mortality. Humans are the only known reservoir for RSV. Spread of the virus from contaminated nasal secretions occurs via large respiratory droplets, so close contact with an infected individual or contaminated surface is required for transmission. RSV can persist for several hours on toys or other objects, which explains the high rate of nosocomial RSV infections, particularly in paediatric wards.

The global annual infection and mortality figures for RSV are estimated to be 64 million and 160,000 respectively. In the U.S. alone RSV is estimated to be responsible for 18,000 to 75,000 hospitalizations and 90 to 1900 deaths annually. In temperate climates, RSV is well documented as a cause of yearly winter epidemics of acute LRI, including bronchiolitis and pneumonia. In the USA, nearly all children have been infected with RSV by two years of age. The incidence rate of RSV-associated LRI in otherwise healthy children was calculated as 37 per 1000 child-year in the first two years of life (45 per 1000 child-year in infants less than 6 months old) and the risk of hospitalization as 6 per 1000 child-years (per 1000 child-years in the first six months of life). Incidence is higher in children with cardio-pulmonary disease and in those born prematurely, who constitute almost half of RSV-related hospital admissions in the USA. Children who experience a more severe LRI caused by RSV later have an increased incidence of childhood asthma. These studies demonstrate widespread need for RSV vaccines, as well as use thereof, in industrialized countries, where the costs of caring for patients with severe LRI and their sequelae are substantial. RSV also is increasingly recognized as an important cause of morbidity from influenza-like illness in the elderly.

Various approaches have been attempted in efforts to produce a safe and effective RSV vaccine that produces durable and protective immune responses in healthy and at risk populations. However, none of the candidates evaluated to date have been proven safe and effective as a vaccine for the purpose of preventing RSV infection and/or reducing or preventing RSV disease, including lower respiratory infections (LRIs).

SUMMARY

This disclosure concerns recombinant respiratory syncytial virus (RSV) antigens. More specifically, this disclosure concerns antigens including a recombinant F protein that has been modified to stabilize the trimeric prefusion conformation. The disclosed recombinant antigens exhibit superior immunogenicity, and are particularly favorably employed as components of immunogenic compositions (e.g., vaccines) for protection against RSV infection and/or disease. Also disclosed are nucleic acids that encode the recombinant antigens, immunogenic compositions containing the antigens, and methods for producing and using the antigens.

BRIEF DESCRIPTION OF THE DRAWINGS

FIG. 1A is a schematic illustration highlighting structural features of the RSV F protein.

FIG. 1B is a schematic illustration of exemplary RSV Prefusion F (PreF) antigens.

FIG. 3 is a bar graph showing neutralization inhibition of human serum by PreF antigen.

FIGS. 4A and B are bar graphs showing serum IgG titers elicited in mice in response to PreF antigen.

FIGS. 5A and B are bar graphs illustrating titers of neutralizing antibodies specific for RSV elicited by PreF antigen.

DETAILED DESCRIPTION

Introduction

Figure 2:
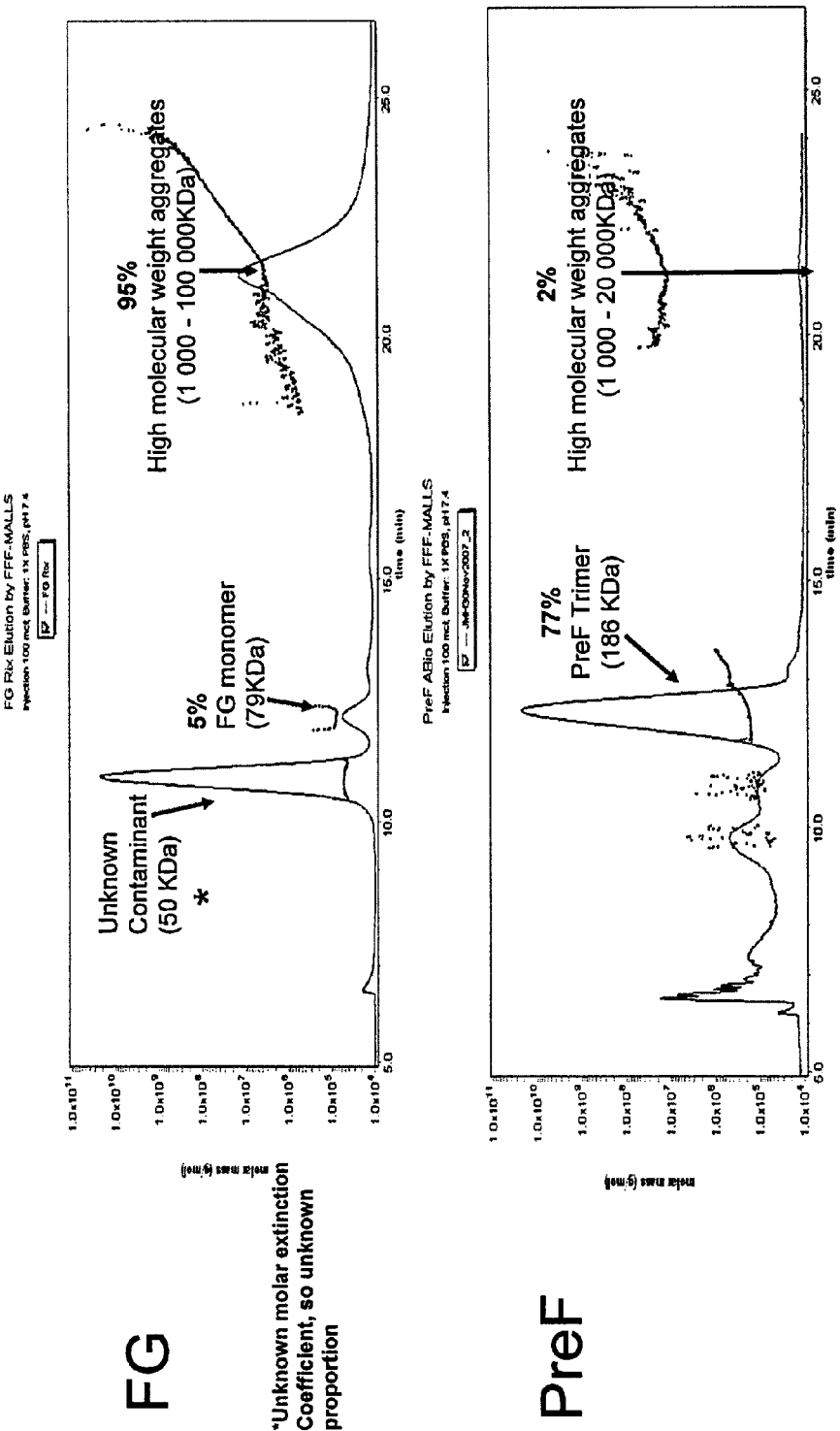
FIG. 2 is a line graph illustrating representative results of asymmetrical field flow fractionation (AFF-MALS) analysis of PreF.

Development of vaccines to prevent RSV infection has been complicated by the fact that host immune responses appear to play a role in the pathogenesis of the disease. Early studies in the 1960s showed that children vaccinated with a formalin-inactivated RSV vaccine suffered from more severe disease on subsequent exposure to the virus as compared to unvaccinated control subjects. These early trials resulted in the hospitalization of 80% of vaccinees and two deaths. The enhanced severity of disease has been reproduced in animal models and is thought to result from inadequate levels of serum-neutralizing antibodies, lack of local immunity, and excessive induction of a type 2 helper T-cell-like (Th2) immune response with pulmonary eosinophilia and increased production of IL-4 and IL-5 cytokines. In contrast, a successful vaccine that protects against RSV infection induces a Th1 biased immune response, characterized by production of IL-2 and γ-interferon (IFN).

The present disclosure concerns recombinant respiratory syncytial virus (RSV) antigens that solve problems encountered with RSV antigens previously used in vaccines, and improve the immunological as well as manufacturing properties of the antigen. The recombinant RSV antigens disclosed herein involve a Fusion (F) protein analog that include a soluble F protein polypeptide, which has been modified to stabilize the prefusion conformation of the F protein, that is, the conformation of the mature assembled F protein prior to fusion with the host cell membrane. These F protein analogs are designated "PreF" or "PreF antigens", for purpose of clarity and simplicity. The PreF antigens disclosed herein are predicated on the unforeseen discovery that soluble F protein analogs that have been modified by the incorporation of a heterologous trimerization domain exhibit improved immunogenic characteristics, and are safe and highly protective when administered to a subject in vivo.

Details of the structure of the RSV F protein are provided herein with reference to terminology and designations widely accepted in the art, and illustrated schematically in FIG. 1A. A schematic illustration of exemplary PreF antigens is provided in FIG. 1B. It will be understood by those of skill in the art that any RSV F protein can be modified to stabilize the prefusion conformation according to the teachings provided herein. Therefore, to facilitate understanding of the principles guiding production of PreF antigens, individual structural components will be indicated with reference to an exemplary F protein, the polynucleotide and amino acid sequence of which are provided in SEQ ID NOs:1 and 2, respectively. Similarly, where applicable, G protein antigens are described in reference to an exemplary G protein, the polynucleotide and amino acid sequences of which are provided in SEQ ID NOs:3 and 4, respectively.

With reference to the primary amino acid sequence of the F protein polypeptide (FIG. 1A), the following terms are utilized to describe structural features of the PreF antigens.

The term F0 refers to a full-length translated F protein precursor. The F0 polypeptide can be subdivided into an F2 domain and an F1 domain separated by an intervening peptide, designated pep27. During maturation, the F0 polypeptide undergoes proteolytic cleavage at two furin sites situated between F2 and F1 and flanking pep27. For purpose of the ensuing discussion, an F2 domain includes at least a portion, and as much as all, of amino acids 1-109, and a soluble portion of an F1 domain includes at least a portion, and up to all, of amino acids 137-526 of the F protein. As indicated above, these amino acid positions (and all subsequent amino acid positions designated herein) are given in reference to the exemplary F protein precursor polypeptide (F0) of SEQ ID NO:2.

The prefusion F (or "PreF") antigen is a soluble (that is, not membrane bound) F protein analog that includes at least one modification that stabilizes the prefusion conformation of the F protein, such that the RSV antigen retains at least one immunodominant epitope of the prefusion conformation of the F protein. The soluble F protein polypeptide includes an F2 domain and an F1 domain of the RSV F protein (but does not include a transmembrane domain of the RSV F protein). In exemplary embodiments, the F2 domain includes amino acids 26-105 and the F1 domain includes amino acids 137-516 of an F protein. However, smaller portions can also be used, so long as the three-dimensional conformation of the stabilized PreF antigen is maintained. Similarly, polypeptides that include additional structural components (e.g., fusion polypeptides) can also be used in place of the exemplary F2 and F1 domains, so long as the additional components do not disrupt the three-dimensional conformation, or otherwise adversely impact stability, production or processing, or decrease immunogenicity of the antigen. The F2 and F1 domains are positioned in an N-terminal to C-terminal orientation designed to replicate folding and assembly of the F protein analog into the mature prefusion conformation. To enhance production, the F2 domain can be preceded by a secretory signal peptide, such as a native F protein signal peptide or a heterologous signal peptide chosen to enhance production and secretion in the host cells in which the recombinant PreF antigen is to be expressed.

The PreF antigens are stabilized (in the trimeric prefusion conformation) by introducing one or more modifications, such as the addition, deletion or substitution, or one or more amino acids. One such stabilizing modification is the addition of an amino acid sequence comprising a heterologous stabilizing domain. In exemplary embodiments, the heterologous stabilizing domain is a protein multimerization domain. One particularly favorable example of such a protein multimerization domain is a coiled-coil domain, such as an isoleucine zipper domain that promotes trimerization of multiple polypeptides having such a domain. An exemplary isoleucine zipper domain is depicted in SEQ ID NO:11. Typically, the heterologous stabilizing domain is positioned C-terminal to the F1 domain.

Optionally, the multimerization domain is connected to the F1 domain via a short amino acid linker sequence, such as the sequence GG. The linker can also be a longer linker (for example, including the sequence GG, such as the amino acid sequence: GGSGGSGGS; SEQ ID NO:14). Numerous conformationally neutral linkers are known in the art that can be used in this context without disrupting the conformation of the PreF antigen.

Another stabilizing modification is the elimination of a furin recognition and cleavage site that is located between the F2 and F1 domains in the native F0protein. One or both furin recognition sites, located at positions 105-109 and at positions 133-136 can be eliminated by deleting or substituting one or more amino acid of the furin recognition sites, such that the protease is incapable of cleaving the PreF polypeptide into its constituent domains. Optionally, the intervening pep27 peptide can also be removed or substituted, e.g., by a linker peptide. Additionally, or optionally, a non-furin cleavage site (e.g., a metalloproteinase site at positions 112-113) in proximity to the fusion peptide can be removed or substituted.

Another example of a stabilizing mutation is the addition or substitution of a hydrophilic amino acid into a hydrophobic domain of the F protein. Typically, a charged amino acid, such as lysine, will be added or substituted for a neutral residue, such as leucine, in the hydrophobic region. For example, a hydrophilic amino acid can be added to, or substituted for, a hydrophobic or neutral amino acid within the HRB coiled-coil domain of the F protein extracellular domain. By way of example, a charged amino acid residue, such as lysine, can be substituted for the leucine present at position 512 of the F protein. Alternatively, or in addition, a hydrophilic amino acid can be added to, or substituted for, a hydrophobic or neutral amino acid within the HRA domain of the F protein. For example, one or more charged amino acids, such as lysine, can be inserted at or near position 105-106 (e.g., following the amino acid corresponding to residue 105 of reference SEQ ID NO:2, such as between amino acids 105 and 106) of the PreF antigen). Optionally, hydrophilic amino acids can be added or substituted in both the HRA and HRB domains. Alternatively, one or more hydrophobic residues can be deleted, so long as the overall conformation of the PreF antigen is not adversely impacted.

Any and/or all of the stabilizing modifications can be used individually and/or in combination with any of the other stabilizing modifications disclosed herein to produce a PreF antigen. In exemplary embodiments the PreF protein comprising a polypeptide comprising an F2 domain and an F1 domain with no intervening furin cleavage site between the F2 domain and the F1 domain, and with a heterologous stabilizing domain (e.g., trimerization domain) positioned C-terminal to the F1 domain. In certain embodiments, the PreF antigen also includes one or more addition and/or substitution of a hydrophilic residue into a hydrophobic HRA and/or HRB domain. Optionally, the PreF antigen has a modification of at least one non-furin cleavage site, such as a metalloproteinase site.

A PreF antigen can optionally include an additional polypeptide component that includes at least an immunogenic portion of the RSV G protein. That is, in certain embodiments, the PreF antigen is a chimeric protein that includes both an F protein and a G protein component. The F protein component can be any of the PreF antigens described above, and the G protein component is selected to be an immunologically active portion of the RSV G protein (up to and/or including a full-length G protein). In exemplary embodiments, the G protein polypeptide includes amino acids 149-229 of a G protein (where the amino acid positions are designated with reference to the G protein sequence represented in SEQ ID NO:4). One of skill in the art will appreciate that a smaller portion or fragment of the G protein can be used, so long as the selected portion retains the dominant immunologic features of the larger G protein fragment. In particular, the selected fragment retains the immunologically dominant epitope between about amino acid positions 184-198 (e.g., amino acids 180-200), and be sufficiently long to fold and assemble into a stable conformation that exhibits the immunodominant epitope. Longer fragments can also be used, e.g., from about amino acid 128 to about amino acid 229, up to the full-length G protein. So long as the selected fragment folds into a stable conformation in the context of the chimeric protein, and does not interfere with production, processing or stability when produced recombinantly in host cells. Optionally, the G protein component is connected to the F protein component via a short amino acid linker sequence, such as the sequence GG. The linker can also be a longer linker (such as the amino acid sequence: GGSGGSGGS: SEQ ID NO:14). Numerous conformationally neutral linkers are known in the art that can be used in this context without disrupting the conformation of the PreF antigen.

Optionally, the G protein component can include one or more amino acid substitutions that reduce or prevent enhanced viral disease in an animal model of RSV disease. That is, the G protein can include an amino acid substitution, such that when an immunogenic composition including the PreF-G chimeric antigen is administered to a subject selected from an accepted animal model (e.g., mouse model of RSV), the subject exhibits reduced or no symptoms of vaccine enhanced viral disease (e.g., eosinophilia, neutrophilia), as compared to a control animal receiving a vaccine including that contains an unmodified G protein. The reduction and/or prevention of vaccine enhanced viral disease can be apparent when the immunogenic compositions are administered in the absence of adjuvant (but not, for example, when the antigens are administered in the presence of a strong Th1 inducing adjuvant). Additionally, the amino acid substitution can reduce or prevent vaccine enhanced viral disease when administered to a human subject. An example of a suitable amino acid substitution is the replacement of asparagine at position 191 by an alanine (Asn→Ala at amino acid 191: N191A).

Optionally, any PreF antigen described above can include an additional sequence that serves as an aid to purification. One example, is a polyhistidine tag. Such a tag can be removed from the final product if desired.

When expressed, the PreF antigens undergo intramolecular folding and assemble into mature protein that includes a multimer of polypeptides. Favorably, the preF antigen polypeptides assemble into a trimer that resembles the prefusion conformation of the mature, processed, RSV F protein.

Any of the PreF antigens (including PreF-G antigens) disclosed herein can be favorably used in immunogenic compositions for the purpose of eliciting a protective immune response against RSV. Such immunogenic compositions typically include a pharmaceutically acceptable carrier and/or excipient, such as a buffer. To enhance the immune response produced following administration, the immunogenic composition typically also includes an adjuvant. In the case of immunogenic compositions for eliciting a protective immune response against RSV (e.g., vaccines), the compositions favorably include an adjuvant that predominantly elicits a Th1 immune response (a Th1 biasing adjuvant). Typically, the adjuvant is selected to be suitable for administration to the target population to which the composition is to be administered. Thus, depending on the application, the adjuvant is selected to be suitable for administration, e.g., to neonates or to the elderly.

The immunogenic compositions described herein are favorably employed as vaccines for the reduction or prevention of infection with RSV, without inducing a pathological response (such as vaccine enhanced viral disease) following administration or exposure to RSV.

In some embodiments, the immunogenic composition includes a PreF antigen (such as the exemplary embodiment illustrated by SEQ ID NO:6) and a second polypeptide that includes a G protein component. The G protein component typically includes at least amino acids 149-229 of a G protein. Although smaller portions of the G protein can be used, such fragments should include, at a minimum, the immunological dominant epitope of amino acids 184-198. Alternatively, the G protein can include a larger portion of the G protein, such as amino acids 128-229 or 130-230, optionally as an element of a larger protein, such as a full-length G protein, or a chimeric polypeptide.

In other embodiments, the immunogenic composition includes a PreF antigen that is a chimeric protein that also includes a G protein component (such as the exemplary embodiments illustrated by SEQ ID NOs:8 and 10). The G protein component of such a chimeric PreF (or PreF-G) antigen typically includes at least amino acids 149-229 of a G protein. As indicated above, smaller or larger fragments (such as amino acids 129-229 or 130-230) of the G protein can also be used, so long as the immunodominant epitopes are retained, and conformation of the PreF-G antigen is not adversely impacted.

Optionally, the immunogenic compositions can also include at least one additional antigen of a pathogenic organism other than RSV. For example, the pathogenic organism is a virus other than RSV, such as Parainfluenza virus (PIV), measles, hepatitis B, poliovirus, or influenza virus. Alternatively, the pathogenic organism can be a bacterium, such as diphtheria, tetanus, pertussis, *Haemophilus influenzae*, and *Pneumococcus*.

Recombinant nucleic acids that encode any of the PreF antigens (including PreF-G antigens) are also a feature of this disclosure. In some embodiments, the polynucleotide sequence of the nucleic acid that encodes the PreF antigen of the nucleic acid is optimized for expression in a selected host (such as CHO cells, other mammalian cells, or insect cells). Accordingly, vectors, including expression vectors (including prokaryotic and eukaryotic expression vectors) are a feature of this disclosure. Likewise, host cells including such nucleic acids, and vectors, are a feature of this disclosure. Such nucleic acids can also be used in the context of immunogenic compositions for administration to a subject to elicit an immune response specific for RSV.

The PreF antigens are favorably used for the prevention and/or treatment of RSV infection. Thus, another aspect of this disclosure concerns a method for eliciting an immune response against RSV. The method involves administering an immunologically effective amount of a composition containing a PreF antigen to a subject (such as a human or animal subject). Administration of an immunologically effective amount of the composition elicits an immune response specific for epitopes present on the PreF antigen. Such an immune response can include B cell responses (e.g., the production of neutralizing antibodies) and/or T cell responses (e.g., the production of cytokines). Favorably, the immune response elicited by the PreF antigen includes elements that are specific for at least one conformational epitope present on the prefusion conformation of the RSV F protein. The PreF antigens and compositions can be administered to a subject without enhancing viral disease following contact with RSV. Favorably, the PreF antigens disclosed herein and suitably formulated immunogenic compositions elicit a Th1 biased immune response that reduces or prevents infection with a RSV and/or reduces or prevents a pathological response following infection with a RSV.

The immunogenic compositions can be administered via a variety of routes, including routes, such as intranasal, that directly place the PreF antigen in contact with the mucosa of the upper respiratory tract. Alternatively, more traditional administration routes can be employed, such an intramuscular route of administration.

Thus, the use of any of the disclosed RSV antigens (or nucleic acids) in the preparation of a medicament for treating RSV infection (for example, prophylactically treating or preventing an RSV infection) is also contemplated. Accordingly, this disclosure provides the disclosed recombinant RSV antigens or the immunogenic compositions for use in medicine, as well as the use thereof for the prevention or treatment of RSV-associated diseases.

Additional details regarding PreF antigens, and methods of using them, are presented in the description and examples below.

Terms

In order to facilitate review of the various embodiments of this disclosure, the following explanations of terms are provided. Additional terms and explanations can be provided in the context of this disclosure.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

Respiratory syncytial virus (RSV) is a pathogenic virus of the family Paramyxoviridae, subfamily Pneumovirinae, genus *Pneumovirus*. The genome of RSV is a negative-sense RNA molecule, which encodes 11 proteins. Tight association of the RNA genome with the viral N protein forms a nucleocapsid wrapped inside the viral envelope. Two groups of human RSV strains have been described, the A and B groups, based on differences in the antigenicity of the G glycoprotein. Numerous strains of RSV have been isolated to date. Exemplary strains indicated by GenBank and/or EMBL Accession number can be found in WO2008114149, which is incorporated herein by reference for the purpose of disclosing the nucleic acid and polypeptide sequences of RSV F and G proteins suitable for use in PreF antigens (including chimeric PreF-G antigens), and in combinations with PreF antigens. Additional strains of RSV are likely to be isolated, and are encompassed within the genus of RSV. Similarly, the genus of RSV encompasses variants arising from naturally occurring (e.g., previously or subsequently identified strains) by genetic drift, or artificial synthesis and/or recombination.

The term "F protein" or "Fusion protein" or "F protein polypeptide" or Fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. Numerous RSV Fusion and Attachment proteins have been described and are known to those of skill in the art. WO2008114149 sets out exemplary F and G protein variants (for example, naturally occurring variants) publicly available as of the filing date of this disclosure.

A "variant" when referring to a nucleic acid or a polypeptide (e.g., an RSV F or G protein nucleic acid or polypeptide, or a PreF nucleic acid or polypeptide) is a nucleic acid or a polypeptide that differs from a reference nucleic acid or polypeptide. Usually, the difference(s) between the variant and the reference nucleic acid or polypeptide constitute a proportionally small number of differences as compared to the referent.

A "domain" of a polypeptide or protein is a structurally defined element within the polypeptide or protein. For example, a "trimerization domain" is an amino acid sequence within a polypeptide that promotes assembly of the polypeptide into trimers. For example, a trimerization domain can promote assembly into trimers via associations with other trimerization domains (of additional polypeptides with the same or a different amino acid sequence). The term is also used to refer to a polynucleotide that encodes such a peptide or polypeptide.

The terms "native" and "naturally occurring" refer to an an element, such as a protein, polypeptide or nucleic acid, that is present in the same state as it is in nature. That is, the element has not been modified artificially. It will be understood, that in the context of this disclosure, there are numerous native/naturally occurring variants of RSV proteins or polypeptides, e.g., obtained from different naturally occurring strains or isolates of RSV.

The term "polypeptide" refers to a polymer in which the monomers are amino acid residues which are joined together through amide bonds. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "fragment," in reference to a polypeptide, refers to a portion (that is, a subsequence) of a polypeptide. The term "immunogenic fragment" refers to all fragments of a polypeptide that retain at least one predominant immunogenic epitope of the full-length reference protein or polypeptide. Orientation within a polypeptide is generally recited in an N-terminal to C-terminal direction, defined by the orientation of the amino and carboxy moieties of individual amino acids. Polypeptides are translated from the N or amino-terminus towards the C or carboxy-terminus.

A "signal peptide" is a short amino acid sequence (e.g., approximately 18-25 amino acids in length) that direct newly synthesized secretory or membrane proteins to and through membranes, e.g., of the endoplasmic reticulum. Signal peptides are frequently but not universally located at the N-terminus of a polypeptide, and are frequently cleaved off by signal peptidases after the protein has crossed the membrane. Signal sequences typically contain three common structural features: an N-terminal polar basic region (n-region), a hydrophobic core, and a hydrophilic c-region).

The terms "polynucleotide" and "nucleic acid sequence" refer to a polymeric form of nucleotides at least 10 bases in length. Nucleotides can be ribonucleotides, deoxyribonucleotides, or modified forms of either nucleotide. The term includes single and double forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. In one embodiment, a polynucleotide encodes a polypeptide. The 5' and 3' direction of a nucleic acid is defined by reference to the connectivity of individual nucleotide units, and designated in accordance with the carbon positions of the deoxyribose (or ribose) sugar ring. The informational (coding) content of a polynucleotide sequence is read in a 5' to 3' direction.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. A "recombinant" protein is one that is encoded by a heterologous (e.g., recombinant) nucleic acid, which has been introduced into a host cell, such as a bacterial or eukaryotic cell. The nucleic acid can be introduced, on an expression vector having signals capable of expressing the protein encoded by the introduced nucleic acid or the nucleic acid can be integrated into the host cell chromosome.

The term "heterologous" with respect to a a nucleic acid, a polypeptide or another cellular component, indicates that the component occurs where it is not normally found in nature and/or that it originates from a different source or species.

The term "purification" (e.g., with respect to a pathogen or a composition containing a pathogen) refers to the process of removing components from a composition, the presence of which is not desired. Purification is a relative term, and does not require that all traces of the undesirable component be removed from the composition. In the context of vaccine production, purification includes such processes as centrifugation, dialization, ion-exchange chromatography, and size-exclusion chromatography, affinity-purification or precipitation. Thus, the term "purified" does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid or protein can be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid or protein content of the preparation.

An "isolated" biological component (such as a nucleic acid molecule, protein or organelle) has been substantially separated or purified away from other biological components in the cell of the organism in which the component naturally occurs, such as, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

An "adjuvant" is an agent that enhances the production of an immune response in a non-specific manner. Common adjuvants include suspensions of minerals (alum, aluminum hydroxide, aluminum phosphate) onto which antigen is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An "immunogenic composition" is a composition of matter suitable for administration to a human or animal subject (e.g., in an experimental setting) that is capable of eliciting a specific immune response, e.g., against a pathogen, such as RSV. As such, an immunogenic composition includes one or more antigens (for example, polypeptide antigens) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., RSV) following exposure of the subject to the pathogen. In the context of this disclosure, the term immunogenic composition will be understood to encompass compositions that are intended for administration to a subject or population of subjects for the purpose of eliciting a protective or palliative immune response against RSV (that is, vaccine compositions or vaccines).

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

A "Th1" biased immune response is characterized by the presence of CD4+ T helper cells that produce IL-2 and IFN-γ, and thus, by the secretion or presence of IL-2 and IFN-γ. In contrast, a "Th2" biased immune response is characterized by a preponderance of CD4+ helper cells that produce IL-4, IL-5, and IL-13.

An "immunologically effective amount" is a quantity of a composition (typically, an immunogenic composition) used to elicit an immune response in a subject to the composition or to an antigen in the composition. Commonly, the desired result is the production of an antigen (e.g., pathogen)-specific immune response that is capable of or contributes to protecting the subject against the pathogen. However, to obtain a protective immune response against a pathogen can require multiple administrations of the immunogenic composition. Thus, in the context of this disclosure, the term immunologically effective amount encompasses a fractional dose that contributes in combination with previous or subsequent administrations to attaining a protective immune response.

The adjective "pharmaceutically acceptable" indicates that the referent is suitable for administration to a subject (e.g., a human or animal subject). Remington's Pharmaceutical Sciences, by E. W. Martin, Mack Publishing Co., Easton, Pa., 15th Edition (1975), describes compositions and formulations (including diluents) suitable for pharmaceutical delivery of therapeutic and/or prophylactic compositions, including immunogenic compositions.

The term "modulate" in reference to a response, such as an immune response, means to alter or vary the onset, magnitude, duration or characteristics of the response. An agent that modulates an immune response alters at least one of the onset, magnitude, duration or characteristics of an immune response following its administration, or that alters at least one of the onset, magnitude, duration or characteristic as compared to a reference agent.

The term "reduces" is a relative term, such that an agent reduces a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, an immunogenic composition that reduces or prevents an infection or a response, such as a pathological response, e.g., vaccine enhanced viral disease, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

A "subject" is a living multi-cellular vertebrate organism. In the context of this disclosure, the subject can be an experimental subject, such as a non-human animal, e.g., a mouse, a cotton rat, or a non-human primate. Alternatively, the subject can be a human subject.

PreF Antigens

In nature, the RSV F protein is expressed as a single polypeptide precursor 574 amino acids in length, designated F0. In vivo, F0 oligomerizes in the endoplasmic reticulum and is proteolytically processed by a furin protease at two conserved furin consensus sequences (furin cleavage sites), RARR$^{109}$ (SEQ ID NO:15) and RKRR$^{136}$ (SEQ ID NO:16) to generate an oligomer consisting of two disulfide-linked fragments. The smaller of these fragments is termed F2 and originates from the N-terminal portion of the F0 precursor. It will be recognized by those of skill in the art that the abbreviations F0, F1 and F2 are commonly designated $F_0$, $F_1$ and $F_2$ in the scientific literature. The larger, C-terminal F1 fragment anchors the F protein in the membrane via a sequence of hydrophobic amino acids, which are adjacent to a 24 amino acid cytoplasmic tail. Three F2-F1 dimers associate to form a mature F protein, which adopts a metastable prefusogenic ("prefusion") conformation that is triggered to undergo a conformational change upon contact with a target cell membrane. This conformational change exposes a hydrophobic sequence, know as the fusion peptide, which associates with the host cell membrane and promotes fusion of the membrane of the virus, or an infected cell, with the target cell membrane.

The F1 fragment contains at least two heptad repeat domains, designated HRA and HRB, and situated in proximity to the fusion peptide and transmembrane anchor domains, respectively. In the prefusion conformation, the F2-F1 dimer forms a globular head and stalk structure, in which the HRA domains are in a segmented (extended) conformation in the globular head. In contrast, the HRB domains form a three-stranded coiled coil stalk extending from the head region. During transition from the prefusion to the postfusion conformations, the HRA domains collapse and are brought into proximity to the HRB domains to form an anti-parallel six helix bundle. In the postfusion state the fusion peptide and transmembrane domains are juxtaposed to facilitate membrane fusion.

Although the conformational description provided above is based on molecular modeling of crystallographic data, the structural distinctions between the prefusion and postfusion conformations can be monitored without resort to crystallography. For example, electron micrography can be used to distinguish between the prefusion and postfusion (alternatively designated prefusogenic and fusogenic) conformations, as demonstrated by Calder et al., *Virology*, 271:122-131 (2000) and Morton et al., *Virology*, 311:275-288, which are incorporated herein by reference for the purpose of their technological teachings. The prefusion conformation can also be distinguished from the fusogenic (postfusion) conformation by liposome association assays as described by Connolly et al., *Proc. Natl. Acad. Sci. USA*, 103:17903-17908 (2006), which is also incorporated herein by reference for the purpose of its technological teachings. Additionally, prefusion and fusogenic conformations can be distinguished using antibodies (e.g., monoclonal antibodies) that specifically recognize conformation epitopes present on one or the other of the prefusion or fusogenic form of the RSV F protein, but not on the other form. Such conformation epitopes can be due to preferential exposure of an antigenic determinant on the surface of the molecule. Alternatively, conformational epitopes can arise from the juxtaposition of amino acids that are non-contiguous in the linear polypeptide.

The PreF antigens disclosed herein are designed to stabilize and maintain the prefusion conformation of the RSV F protein, such that in a population of expressed protein, a substantial portion of the population of expressed protein is in the prefusogenic (prefusion) conformation (e.g., as predicted by structural and/or thermodynamic modeling or as assessed by one or more of the methods disclosed above). Stabilizing modifications are introduced into a native (or synthetic) F protein, such as the exemplary F protein of SEQ ID NO:2, such that the major immunogenic epitopes of the prefusion conformation of the F protein are maintained following introduction of the PreF antigen into a cellular or extracellular environment (for example, in vivo, e.g., following administration to a subject).

First, a heterologous stabilizing domain can be placed at the C-terminal end of the construct in order to replace the membrane anchoring domain of the F0 polypeptide. This stabilizing domain is predicted to compensate for the HRB instability, helping to stabilize the prefusion conformer. In exemplary embodiments, the heterologous stabilizing domain is a protein multimerization domain. One particularly favorable example of such a protein multimerization domain is a trimerization domain. Exemplary trimerization domains fold into a coiled-coil that promotes assembly into trimers of multiple polypeptides having such coiled-coil domains. One favorable example of a trimerization domain is an isoleucine zipper. An exemplary isoleucine zipper domain is the engineered yeast GCN4 isoleucine variant described by Harbury et al. *Science* 262:1401-1407 (1993). The sequence of one suitable isoleucine zipper domain is represented by SEQ ID NO:11, although variants of this sequence that retain the ability to form a coiled-coil stabilizing domain are equally suitable. Alternative stabilizing coiled coil trimerization domains include: TRAF2 (GENBANK® Accession No. Q12933 [gi:23503103]; amino acids 299-348); Thrombospondin 1 (Accession No. PO7996 [gi:135717]; amino acids 291-314); Matrilin-4 (Accession No. O95460 [gi:14548117]; amino acids 594-618; CMP (matrilin-1) (Accession No. NP_002370 [gi:4505111]; amino acids 463-496; HSF1 (Accession No. AAX42211 [gi:61362386]; amino acids 165-191; and Cubilin (Accession No. NP_001072 [gi:4557503]; amino acids 104-138. It is expected that a suitable trimerization domain results in the assembly of a substantial portion of the expressed protein into trimers. For example, at least 50% of a recombinant PreF polypeptide having a trimerization domain will assemble into a trimer (e.g., as assessed by AFF-MALS). Typically, at least 60%, more favorably at least 70%, and most desirably at least about 75% or more of the expressed polypeptide exists as a trimer.

In order to stabilize HRB even more, the leucine residue located at position 512 (relative to the native F0 protein) of the PreF can be substituted by a lysine (L482K of the exemplary PreF antigen polypeptide of SEQ ID NO:6). This substitution improves the coiled coil hydrophobic residue periodicity. Similarly, a lysine can be added following the amino acid at position 105.

Secondly, pep27 can be removed. Analysis of a structural model of the RSV F protein in the prefusion state suggests that pep27 creates a large unconstrained loop between F1 and F2. This loop does not contribute to stabilization of the prefusion state, and is removed following cleavage of the native protein by furin.

Third, one or both furin cleavage motifs can be deleted. With this design, the fusion peptide is not cleaved from F2, preventing release from the globular head of the prefusion conformer and accessibility to nearby membranes. Interaction between the fusion peptide and the membrane interface is predicted to be a major issue in the prefusion state instability. During the fusion process, interaction between the fusion peptide and the target membrane results in the exposure of the fusion peptide from within the globular head structure, enhancing instability of the prefusion state and folding into post-fusion conformer. This conformation change enables the process of membrane fusion. Removal of one or both of the furin cleavage sites is predicted to prevent membrane accessibility to the N-terminal part of the fusion peptide, stabilizing the prefusion state.

Optionally, at least one non-furin cleavage site can also be removed, for example by substitution of one or more amino acids. For example, experimental evidence suggests that under conditions conducive to cleavage by certain metalloproteinases, the PreF antigen can be cleaved in the vicinity of amino acids 110-118 (for example, with cleavage occurring between amino acids 112 and 113 of the PreF antigen; between a leucine at position 142 and glycine at position 143 of the reference F protein polypeptide of SEQ ID NO:2). Accordingly, modification of one or more amino acids within this region can reduce cleavage of the PreF antigen. For example, the leucine at position 112 can be substituted with a different amino acid, such as isoleucine or tryptophan. Alternatively or additionally, the glycine at position 113 can be substituted by a serine or alanine.

The native F protein polypeptide can be selected from any F protein of an RSV A or RSV B strain, or from variants thereof (as defined above). In certain exemplary embodiments, the F protein polypeptide is the F protein represented by SEQ ID NO:2. To facilitate understanding of this disclosure, all amino acid residue positions, regardless of strain, are given with respect to (that is, the amino acid residue position corresponds to) the amino acid position of the exemplary F protein. Comparable amino acid positions of any other RSV A or B strain can be determined easily by those of ordinary skill in the art by aligning the amino acid sequences of the selected RSV strain with that of the exemplary sequence using readily available and well-known alignment algorithms (such as BLAST, e.g., using default parameters). Numerous additional examples of F protein polypeptides from different RSV strains are disclosed in WO2008114149 (which is incorporated herein by reference for the purpose of providing additional examples of RSV F and G protein sequences). Additional variants can arise through genetic drift, or can be produced artificially using site directed or random mutagenesis, or by recombination of two or more preexisting variants. Such additional variants are also suitable in the context of the PreF (and PreF-G) antigens disclosed herein.

In selecting F2 and F1 domains of the F protein, one of skill in the art will recognize that it is not strictly necessary to include the entire F2 and/or F1 domain. Typically, conformational considerations are of importance when selecting a subsequence (or fragment) of the F2 domain. Thus, the F2 domain typically includes a portion of the F2 domain that facilitates assembly and stability of the polypeptide. In certain exemplary variants, the F2 domain includes amino acids 26-105. However, variants having minor modifications in length (by addition, or deletion of one or more amino acids) are also possible.

Typically, at least a subsequence (or fragment) of the F1 domain is selected and designed to maintain a stable conformation that includes immunodominant epitopes of the F protein. For example, it is generally desirable to select a subsequence of the F1 polypeptide domain that includes epitopes recognized by neutralizing antibodies in the regions of amino acids 262-275 (palivizumab neutralization) and 423-436 (Centocor's ch101F MAb). Additionally, desirable to include T cell epitopes, e.g., in the region of animo acids 328-355. Most commonly, as a single contiguous portion of the F1 subunit (e.g., spanning amino acids 262-436) but epitopes could be retained in a synthetic sequence that includes these immunodominant epitopes as discontinuous elements assembled in a stable conformation. Thus, an F1 domain polypeptide comprises at least about amino acids 262-436 of an RSV F protein polypeptide. In one non-limiting example provided herein, the F1 domain comprises amino acids 137 to 516 of a native F protein polypeptide. One of skill in the art will recognize that additional shorter subsequences can be used at the discretion of the practitioner.

When selecting a subsequence of the F2 or F1 domain (or as will be discussed below with respect to the G protein component of certain PreF-G antigens), in addition to conformational consideration, it can be desirable to choose sequences (e.g., variants, subsequences, and the like) based on the inclusion of additional immunogenic epitopes. For example, additional T cell epitopes can be identified using anchor motifs or other methods, such as neural net or polynomial determinations, known in the art, see, e.g., RANKPEP (available on the world wide web at: mif.dfci.harvard.edu/Tools/rankpep.html); ProPredI (available on the world wide web at: imtech.res.in/raghava/propredI/index.html); Bimas (available on the world wide web at: www-bimas.dcrt.nih.gov/molbi/hla_bind/index.html); and SYFPEITH (available on the world wide web at: syfpeithi.bmi-heidelberg.com/scripts/MHCServer.dll/home.htm). For example, algorithms are used to determine the "binding threshold" of peptides, and to select those with scores that give them a high probability of MHC or antibody binding at a certain affinity. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide.

Anchor residues are conserved residues that provide a contact point with the MHC molecule. T cell epitopes identified by such predictive methods can be confirmed by measuring their binding to a specific MHC protein and by their ability to stimulate T cells when presented in the context of the MHC protein.

Favorably, the PreF antigens (including PreF-G antigens as discussed below) include a signal peptide corresponding to the expression system, for example, a mammalian or viral signal peptide, such as an RSV F0 native signal sequence (e.g., amino acids 1-25 of SEQ ID NO:2 or amino acids 1-25 of SEQ ID NO:6). Typically, the signal peptide is selected to be compatible with the cells selected for recombinant expression. For example, a signal peptide (such as a baculovirus signal peptide, or the melittin signal peptide, can be substituted for expression, in insect cells. Suitable plant signal peptides are known in the art, if a plant expression system is preferred. Numerous exemplary signal peptides are known in the art, (see, e.g., see Zhang & Henzel, *Protein Sci.*, 13:2819-2824 (2004), which describes numerous human signal peptides) and are catalogued, e.g., in the SPdb signal peptide database, which includes signal sequences of archaea, prokaryotes and eukaryotes (http://proline.bic.nus.edu.sg/spdb/). Optionally, any of the preceding antigens can include an additional sequence or tag, such as a His-tag to facilitate purification.

Optionally, the PreF antigen can include additional immunogenic components. In certain particularly favorable embodiments, the PreF antigen includes an RSV G protein antigenic component. Exemplary chimeric proteins having a PreF and G component include the following PreF_V1 (represented by SEQ ID NOs:7 and 8) and PreF_V2 (represented by SEQ ID NOs:9 and 10).

In the PreF-G antigens, an antigenic portion of the G protein (e.g., a truncated G protein, such as amino acid residues 149-229) is added at the C-terminal end of the construct. Typically, the G protein component is joined to the F protein component via a flexible linker sequence. For example, in the exemplary PreF_V1 design, the G protein is joined to the PreF component by a -GGSGGSGGS- linker (SEQ ID NO:14). In the PreF_V2 design, the linker is shorter. Instead of having the -GGSGGSGGS- linker (SEQ ID NO:14), PreF_V2 has 2 glycines (-GG-) for linker.

Where present, the G protein polypeptide domain can include all or part of a G protein selected from any RSV A or RSV B strain. In certain exemplary embodiments, the G protein is (or is 95% identical to) the G protein represented by SEQ ID NO:4. Additional examples of suitable G protein sequences can be found in WO2008114149 (which is incorporated herein by reference).

The G protein polypeptide component is selected to include at least a subsequence (or fragment) of the G protein that retains the immunodominant T cell epitope(s), e.g., in the region of amino acids 183-197, such as fragments of the G protein that include amino acids 151-229, 149-229, or 128-229 of a native G protein. In one exemplary embodiment, the G protein polypeptide is a subsequence (or fragment) of a native G protein polypeptide that includes all or part of amino acid residues 149 to 229 of a native G protein polypeptide. One of skill in the art will readily appreciate that longer or shorter portions of the G protein can also be used, so long as the portion selected does not conformationally destabilize or disrupt expression, folding or processing of the PreF-G antigen. Optionally, the G protein domain includes an amino acid substitution at position 191, which has previously been shown to be involved in reducing and/or preventing enhanced disease characterized by eosinophilia associated with formalin inactivated RSV vaccines. A thorough description of the attributes of naturally occurring and substituted (N191A) G proteins can be found, e.g., in US Patent Publication No. 2005/0042230, which is incorporated herein by reference.

For example, with respect to selection of sequences corresponding to naturally occurring strains, one or more of the domains can correspond in sequence to an RSV A or B strain, such as the common laboratory isolates designated A2 or Long, or any other naturally occurring strain or isolate (as disclosed in the aforementioned WO2008114149). In addition to such naturally occurring and isolated variants, engineered variants that share sequence similarity with the aforementioned sequences can also be employed in the context of PreF (including PreF-G) antigens. It will be understood by those of skill in the art, that the similarity between PreF antigen polypeptide (and polynucleotide sequences as described below), as for polypeptide (and nucleotide sequences in general), can be expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid (or polynucleotide) sequences, the more similar are the higher order structures resulting from folding and assembly. Variants of a PreF polypeptide (and polynucleotide) sequences typically have one or a small number of amino acid deletions, additions or substitutions but will nonetheless share a very high percentage of their amino acid, and generally their polynucleotide sequence. More importantly, the variants retain the structural and, thus, conformational attributes of the reference sequences disclosed herein.

Methods of determining sequence identity are well known in the art, and are applicable to PreF antigen polypeptides, as well as the nucleic acids that encode them (e.g., as described below). Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

In some instances, the PreF antigens has one or more amino acid modification relative to the amino acid sequence of the naturally occurring strain from which it is derived (e.g., in addition to the aforementioned stabilizing modifications). Such differences can be an addition, deletion or substitution of one or more amino acids. A variant typically differs by no more than about 1%, or 2%, or 5%, or 10%, or 15%, or 20% of the amino acid residues. For example, a variant PreF antigen (including PreF-G) polypeptide sequence can include 1, or 2, or up to 5, or up to about 10, or up to about 15, or up to about 50, or up to about 100 amino acid differences as compared to the exemplary PreF antigen polypeptide sequences of SEQ ID NOs:6, 8, and/or 10. Thus, a variant in the context of an RSV F or G protein, or PreF antigen (including PreF-G antigen), typically shares at least 80%, or 85%, more commonly, at least about 90% or more, such as 95%, or even 98% or 99% sequence identity with a reference protein, e.g., the reference sequences illustrated in SEQ ID NO:2, 4, 6, 8 and/or 10, or any of the exemplary PreF antigens disclosed herein. Additional variants included as a feature of this disclosure are PreF antigens (including PreF-G antigens) that include all or part of a nucleotide or amino acid sequence selected from the naturally occurring variants disclosed in WO2008114149. Additional variants can arise through genetic drift, or can be produced artificially using site directed or random mutagenesis, or by recombination of two or more preexisting variants. Such additional variants are also suitable in the context of the PreF (and PreF-G) antigens disclosed herein. For example, the modification can be a substitution of one or more amino acids (such as two amino acids, three amino acids, four amino acids, five amino acids, up to about ten amino acids, or more) that do not alter the conformation or immunogenic epitopes of the resulting PreF antigen.

Alternatively or additionally, the modification can include a deletion of one or more amino acids and/or an addition of one or more amino acids. Indeed, if desired, one or more of the polypeptide domains can be a synthetic polypeptide that does not correspond to any single strain, but includes component subsequences from multiple strains, or even from a consensus sequence deduced by aligning multiple strains of RSV virus polypeptides. In certain embodiments, one or more of the polypeptide domains is modified by the addition of an amino acid sequence that constitutes a tag, which facilitates subsequent processing or purification. Such a tag can be an antigenic or epitope tag, an enzymatic tag or a polyhistidine tag. Typically the tag is situated at one or the other end of the protein, such as at the C-terminus or N-terminus of the antigen or fusion protein.

Nucleic Acids that Encode PreF Antigens

Another aspect of this disclosure concerns recombinant nucleic acids that encode PreF antigens as described above. In certain embodiments, the recombinant nucleic acids are codon optimized for expression in a selected prokaryotic or eukaryotic host cell. For example, SEQ ID NOs: 5 and 12 are two different illustrative, non-limiting, examples of sequences that encode a PreF antigen, which have been codon optimized for expression in mammalian, e.g., CHO, cells. To facilitate replication and expression, the nucleic acids can be incorporated into a vector, such as a prokaryotic or a eukaryotic expression vector. Host cells including recombinant PreF antigen-encoding nucleic acids are also a feature of this disclosure. Favorable host cells include prokaryotic (i.e., bacterial) host cells, such as *E. coli*, as well as numerous eukaryotic host cells, including fungal (e.g., yeast) cells, insect cells, and mammalian cells (such as CHO, VERO and HEK293cells).

To facilitate replication and expression, the nucleic acids can be incorporated into a vector, such as a prokaryotic or a eukaryotic expression vector. Although the nucleic acids disclosed herein can be included in any one of a variety of vectors (including, for example, bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others), most commonly the vector will be an expression vector suitable for generating polypeptide expression products. In an expression vector, the nucleic acid encoding the PreF antigen is typically arranged in proximity and orientation to an appropriate transcription control sequence (promoter, and optionally, one or more enhancers) to direct mRNA synthesis. That is, the polynucleotide sequence of interest is operably linked to an appropriate transcription control sequence. Examples of such promoters include: the immediate early promoter of CMV, LTR or SV40 promoter, polyhedrin promoter of baculovirus, *E. coli* lac or trp promoter, phage T7 and lambda $P_L$ promoter, and other promoters known to control expression of genes in prokaryotic or eukaryotic cells or their viruses. The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as kanamycin, tetracycline or ampicillin resistance in *E. coli.*

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide-coding sequence, or a portion thereof, is inserted, exogenous translational control signals, including an ATG initiation codon is provided for translation of the nucleic acid encoding PreF antigen. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use (Scharf et al. (1994) *Results Probl Cell Differ* 20:125-62; Bitter et al. (1987) *Methods in Enzymol* 153:516-544).

In some instances, the nucleic acid (such as a vector) that encodes the PreF antigen includes one or more additional sequence elements selected to increase and/or optimize expression of the PreF encoding nucleic acid when introduced into a host cell. For example, in certain embodiments, the nucleic acids that encode the PreF antigen include an intron sequence, such as a Human Herpesvirus 5 intron sequence (see, e.g., SEQ ID NO:13). Introns have been repeatedly demonstrated to enhance expression of homologous and heterologous nucleic acids when appropriately positioned in a recombinant construct. Another class of expression-enhancing sequences includes an epigenetic element such as a Matrix Attachment Region (or MAR), or a similar epigenetic element, e.g., STAR elements (for example, such as those STAR elements disclosed in Otte et al., *Biotechnol. Prog.* 23:801-807, 2007). Without being bound by theory, MARs are believed to mediate the anchorage of a target DNA sequence to the nuclear matrix, generating chromatin loop domains that extend outwards from the heterochromatin cores. While MARs do not contain any obvious consensus or recognizable sequence, their most consistent feature appears to be an overall high A/T content, and C bases predominating on one strand. These regions appear to form bent secondary structures that may be prone to strand separation, and may include a core-unwinding element (CUE) that can serve as the nucleation point for strand separation. Several simple AT-rich sequence motifs have been associated with MAR sequences: e.g., the A-box, the T-box, DNA unwinding motifs, SATB1 binding sites (H-box, A/T/C25) and consensus Topoisomerase II sites for vertebrates or Drosophila. Exemplary MAR sequences are described in published US patent application no. 20070178469, and in international patent application no. WO02/074969 (which are incorporated herein by reference). Additional MAR sequences that can be used to enhance expression of a nucleic acid encoding a PreF antigen include chicken lysozyme MAR, MARp1-42, MARp1-6, MARp1-68, and MARpx-29, described in Girod et al., *Nature Methods*, 4:747-753, 2007 (disclosed in GenBank Accession Nos. EA423306, DI107030, DI106196, DI107561, and DI106512, respectively). One of skill will appreciate that expression can further be modulated be selecting a MAR that produces an intermediate level of enhancement, as is reported for MAR 1-9. If desired, alternative MAR sequences for increasing expression of a PreF antigen can be identified by searching sequence databases, for example, using software such as MAR-Finder (available on the web at futuresoft.org/MarFinder), SMARTest (available on the web at genomatix.de), or SMARScan I (Levitsky et al., *Bioinformatics* 15:582-592, 1999). In certain embodiments, the MAR is introduced (e.g., transfected) into the host cell on the same nucleic acid (e.g., vector) as the PreF antigen-encoding sequence. In an alternative embodiment, the MAR is introduced on a separate nucleic acid (e.g., in trans) and it can optionally cointegrate with the PreF antigen-encoding polynucleotide sequence.

Exemplary procedures sufficient to guide one of ordinary skill in the art through the production of recombinant PreF antigen nucleic acids can be found in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

Exemplary nucleic acids that encode PreF antigen polypeptides are represented by SEQ ID NOs: 5, 7, 9, 12 and 13. Additional variants of can be produced by assembling analogous F and G protein polypeptide sequences selected from any of the known (or subsequently) discovered strains of RSV, e.g., as disclosed in WO2008114149. Additional sequence variants that share sequence identity with the exemplary variants can be produced by those of skill in the art. Typically, the nucleic acid variants will encode polypeptides that differ by no more than 1%, or 2%, or 5%, or 10%, or 15%, or 20% of the amino acid residues. That is, the encoded polypeptides share at least 80%, or 85%, more commonly, at least about 90% or more, such as 95%, or even 98% or 99% sequence identity. It will be immediately understood by those of skill in the art, that the polynucleotide sequences encoding the PreF polypeptides, can themselves share less sequence identity due to the redundancy of the genetic code. In some instances, the PreF antigens has one or more amino acid modification relative to the amino acid sequence of the naturally occurring strain from which it is derived (e.g., in addition to the aforementioned stabilizing modifications). Such differences can be an addition, deletion or substitution of one or more nucleotides or amino acids, respectively. A variant typically differs by no more than about 1%, or 2%, or 5%, or 10%, or 15%, or 20% or of the nucleotide residues. For example, a variant PreF antigen (including PreF-G) nucleic acid can include 1, or 2, or up to 5, or up to about 10, or up to about 15, or up to about 50, or up to about 100 nucleotide differences as compared to the exemplary PreF antigen nucleic acids of SEQ ID NOs: 5, 7, 9, 12 and/or 13. Thus, a variant in the context of an RSV F or G protein, or PreF antigen (including PreF-G antigen) nucleic acid, typically shares at least 80%, or 85%, more commonly, at least about 90% or more, such as 95%, or even 98% or 99% sequence identity with a reference sequence, e.g., the reference sequences illustrated in SEQ ID NO:1, 3, 5, 7, 9, 12 or 13, or any of the other exemplary PreF antigen nucleic acids disclosed herein. Additional variants included as a feature of this disclosure are PreF antigens (including PreF-G antigens) that include all or part of a nucleotide sequence selected from the naturally occurring variants disclosed in WO2008114149. Additional variants can arise through genetic drift, or can be produced artificially using site directed or random mutagenesis, or by recombination of two or more preexisting variants. Such additional variants are also suitable in the context of the PreF (and PreF-G) antigens disclosed herein.

In addition to the variant nucleic acids previously described, nucleic acids that hybridize to one or more of the exemplary nucleic acids represented by SEQ ID NOs:1, 3, 5, 7, 9, 12 and 13 can also be used to encode PreF antigens. One of skill in the art will appreciate that in addition to the % sequence identity measure discussed above, another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993 and Ausubel et al. *Short Protocols in Molecular Biology*, 4$^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast, nucleic acids that hybridize under "low stringency conditions include those with much less sequence identity, or with sequence identity over only short subsequences of the nucleic acid. It will, therefore, be understood that the various variants of nucleic acids that are encompassed by this disclosure are able to hybridize to at least one of SEQ ID NOs:1, 3, 5, 7, 9, and/or 12 over substantially their entire length.

Methods of Producing RSV Antigenic Polypeptides

The PreF antigens (including PreF-G antigens, and also where applicable, G antigens) disclosed herein are produced using well established procedures for the expression and purification of recombinant proteins. Procedures sufficient to guide one of skill in the art can be found in the following references: Sambrook et al., *Molecular Cloning: A Laboratory Manual*, Cold Spring Harbor Laboratory Press, Cold Spring Harbor, N.Y., 200; and Ausubel et al. *Short Protocols in Molecular Biology*, 4$^{th}$ ed., John Wiley & Sons, Inc., 999. Additional and specific details are provided hereinbelow.

Recombinant nucleic acids that encode the PreF antigens are introduced into host cells by any of a variety of well-known procedures, such as electroporation, liposome mediated transfection (e.g., using a commercially available liposomal transfection reagent, such as LIPOFECTAMINE™2000 or TRANSFECTIN™), Calcium phosphate precipitation, infection, transfection and the like, depending on the selection of vectors and host cells. Exemplary nucleic acids that encode PreF antigens (including PreF-G antigens) are provided in SEQ ID NOs:5, 7, 9, 12 and 13. One of skill in the art will appreciate that SEQ ID NOs:5, 7, 9, 12 and 13 are illustrative and not intended to be limiting. For example, polynucleotide sequences that encode the same proteins as SEQ ID NOs:5, 7 and 9, (e.g., represented by SEQ ID NOs: 6, 8 and 10), but that differ only by the redundancy of the genetic code (such as by alternative codon optimization, as shown in SEQ ID NO:12), can easily be used instead of the exemplary sequences of SEQ ID NOs:5, 7, and 9. Similarly, polynucleotide sequences that include expression-enhancing elements, such as internally positioned introns (or by the addition of promoter, enhancer, intron or other similar elements), as illustrated in SEQ ID NO:13, can be employed. One of ordinary skill in the art will recognize that combinations of such modifications are likewise suitable. Similarly, homologous sequences selected from any RSV A or RSV B strain, and/or other sequences that share substantial sequence identity, as discussed above, can also be used to express PreF antigens. Indeed, any of the variant nucleic acids previously disclosed can suitably be introduced into host cells and used to produce PreF antigens (including PreF-G antigens) and where applicable G polypeptides.

Host cells that include recombinant PreF antigen-encoding nucleic acids are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO and HEK293 cells). Recombinant PreF antigen nucleic acids are introduced (e.g., transduced, transformed or transfected) into host cells, for example, via a vector, such as an expression vector. As described above, the vector is most typically a plasmid, but such vectors can also be, for example, a viral particle, a phage, etc. Examples of appropriate expression hosts include: bacterial cells, such as *E. coli, Streptomyces*, and *Salmonella typhimurium;* fungal cells, such as *Saccharomyces cerevisiae, Pichia pastoris*, and *Neurospora crassa;* insect cells such as *Drosophila* and *Spodoptera frugiperda;* mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein. Expression products corresponding to the nucleic acids of the invention can also be produced in non-animal cells such as plants, yeast, fungi, bacteria and the like. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture; Fundamental Methods* Springer Lab Manual, Springer-Verlag (Berlin Heidelberg New York) and Atlas and Parks (eds) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors which direct high level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wiss.), in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. For reviews, see Berger, Ausubel, and, e.g., Grant et al. (1987; *Methods in Enzymology* 153:516-544). In mammalian host cells, a number of expression systems, including both plasmis and viral-based systems, can be utilized.

A host cell is optionally chosen for its ability to modulate the expression of the inserted sequences or to process the expressed protein in the desired fashion. Such modifications of the protein include, but are not limited to, glycosylation, (as well as, e.g., acetylation, carboxylation, phosphorylation, lipidation and acylation). Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant PreF antigens disclosed herein, stable expression systems are typically used. For example, cell lines which stably express a PreF antigen polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding a PreF antigen are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. Optionally, the medium includes components and/or additives that decrease degradation of expressed proteins by proteinases. For example, the medium used for culturing cells to produce PreF antigen can include a protease inhibitor, such as a chelating agent or small molecule inhibitor (e.g., AZ11557272, AS111793, etc.), to reduce or eliminate undesired cleavage by cellular, or extracellular (e.g., matrix) proteinases.

The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed PreF antigens can be recovered and purified from recombinant cell cultures by any of a number of methods well known in the art, including ammonium sulfate or ethanol precipitation, acid extraction, filtration, ultrafiltration, centrifugation, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art, including, e.g., those set forth in Sandana (1997) *Bioseparation of Proteins*, Academic Press, Inc.; and Bollag et al. (1996) *Protein Methods*, $2^{nd}$ Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, U.K.; Scopes (1993) *Protein Purification: Principles and Practice* $3^{rd}$ Edition Springer Verlag, NY; Janson and Ryden (1998) *Protein Purification: Principles, High Resolution Methods and Applications*, Second Edition Wiley-VCH, NY; and Walker (1998) *Protein Protocols on CD-ROM* Humana Press, NJ.

In certain examples, the nucleic acids are introduced into cells via vectors suitable for introduction and expression in prokaryotic cells, e.g., *E. coli* cells. For example, a nucleic acid including a polynucleotide sequence that encodes a PreF antigen can be introduced into any of a variety of commercially available or proprietary vectors, such as the pET series of expression vectors (e.g., pET9b and pET2d). Expression of the coding sequence is inducible by IPTG, resulting in high levels of protein expression. The polynucleotide sequence encoding the PreF antigen is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, the Rosetta and BL21 (DE3) strains have proven favorable for expression of recombinant vectors containing polynucleotide sequences that encode PreF antigens.

More typically, the polynucleotides that encode the PreF antigens are incorporated into expression vectors that are suitable for introduction and expression in eukaryotic (e.g., insect or mammalian cells). Favorably, such nucleic acids are codon optimized for expression in the selected vector/host cell (for example, the sequences illustrated in SEQ ID NOs:5, 7, 9 and 12 are codon optimized for expression in CHO cells). In one exemplary embodiment, the polynucleotide sequence that encodes the PreF antigen is introduced into a vector, such as the pEE14 vector developed by Lonza Biologicals firm. The polypeptide is expressed under a constitutive promoter, such as the immediate early CMV (CytoMegaloVirus) promoter. Selection of the stably transfected cells expressing the polypeptide is made based on the ability of the transfected cells to grow in the absence of a glutamine source. Cells that have successfully integrated the pEE14 are able to grow in the absence of exogenous glutamine, because the pEE 14 vector expresses the GS (Glutamine Synthetase) enzyme. Selected cells can be clonally expanded and characterized for expression of the desired PreF polypeptide.

In another example, the polynucleotide sequence that encodes the PreF antigen is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the antigen is inserted into the pAcSG2 transfer vector. Then, host cells SF9 (*Spodoptera frugiperda*) are co-transfected by pAcSG2-chimeric plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the PreF antigen is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the Sf9, and the High Five cell line derived from a cabbage looper, *Trichoplusia ni*.

Following transfection and induction of expression (according to the selected promoter and/or enhancers or other regulatory elements), the expressed polypeptides are recovered (e.g., purified or enriched) and renatured to ensure folding into an antigenically active prefusion conformation.

Immunogenic Compositions and Methods

Also provided are immunogenic compositions including any of the PreF antigens disclosed above (such as those exemplified by SEQ ID NOs: 6, 8 and 10) and a pharmaceutically acceptable carrier or excipient.

In certain embodiments, typically, embodiments in which the PreF antigen does not include a G protein component (such as SEQ ID NO:6), the immunogenic composition can include an isolated, recombinant and/or purified G protein. Numerous suitable G proteins have been described in the art, and include full length recombinant G proteins and chimeric proteins made up of a portion of the G protein (such as amino acids 128-229 or 130-230) and a fusion partner (such as thioredoxin), or a signal and/or leader sequence, that facilitates expression and/or purification. Exemplary G proteins for use in admixture with a PreF antigen can be found in WO2008114149, U.S. Pat. No. 5,149,650, U.S. Pat. No. 6,113,911, US Published Application No. 20080300382, and U.S. Pat. No. 7,368,537, each of which is incorporated herein by reference. As indicated with respect to the chimeric PreF-G proteins, a smaller fragment of the G protein, such as the portion between amino acids 149-229, or the portion between approximately 128 to approximately 229 can favorably be employed in the context of mixtures involving a PreF (without G) and G. As discussed above, the important consideration is the presence of immunodominant epitopes, e.g., included within the region of amino acids 183-197. Alternatively, a full-length G protein can be employed in such compositions.

Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in *Remington's Pharmaceutical Sciences*, by E. W. Martin, Mack Publishing Co., Easton, Pa., 5th Edition (975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroyl-sarcosine sodium salt, L-proline, Non detergent sulfobetaine, Guanidine hydrochloride, Urea, Trimethylamine oxide, KCl, $Ca^{2+}$, $Mg^{2+}$, $Mn^{2+}$, $Zn^{2+}$ and other divalent cation related salts, Dithiothreitol, Dithioerytrol, and β-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Optionally, the immunogenic compositions also include an adjuvant. In the context of an immunogenic composition suitable for administration to a subject for the purpose of eliciting a protective immune response against RSV, the adjuvant is selected to elicit a Th1 biased immune response.

The adjuvant is typically selected to enhance a Th1 biased immune response in the subject, or population of subjects, to whom the composition is administered. For example, when the immunogenic composition is to be administered to a subject of a particular age group susceptible to (or at increased risk of) RSV infection, the adjuvant is selected to be safe and effective in the subject or population of subjects. Thus, when formulating an immunogenic composition containing an RSV PreF antigen for administration in an elderly subject (such as a subject greater than 65 years of age), the adjuvant is selected to be safe and effective in elderly subjects. Similarly, when the immunogenic composition containing the RSV PreF antigen is intended for administration in neonatal or infant subjects (such as subjects between birth and the age of two years), the adjuvant is selected to be safe and effective in neonates and infants.

Additionally, the adjuvant is typically selected to enhance a Th1 immune response when administered via a route of administration, by which the immunogenic composition is administered. For example, when formulating an immunogenic composition containing a PreF antigen for nasal administration, proteosome and protollin are favorable Th1-biasing adjuvants. In contrast, when the immunogenic composition is formulated for intramuscular administration, adjuvants including one or more of 3D-MPL, squalene (e.g., QS21), liposomes, and/or oil and water emulsions are favorably selected.

One suitable adjuvant for use in combination with PreF antigens is a non-toxic bacterial lipopolysaccharide derivative. An example of a suitable non-toxic derivative of lipid A, is monophosphoryl lipid A or more particularly 3-Deacylated monophoshoryl lipid A (3D-MPL). 3D-MPL is sold under the name MPL by GlaxoSmithKline Biologicals N.A., and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL can be used. Small particle 3D-MPL has a particle size such that it can be sterile-filtered through a 0.22 µm filter. Such preparations are described in WO94/21292.

A lipopolysaccharide, such as 3D-MPL, can be used at amounts between 1 and 50 µg, per human dose of the immunogenic composition. Such 3D-MPL can be used at a level of about 25 µg, for example between 20-30 µg, suitably between 21-29 µg or between 22 and 28 µg or between 23 and 27 µg or between 24 and 26 µg, or 25 µg. In another embodiment, the human dose of the immunogenic composition comprises 3D-MPL at a level of about 10 µg, for example between 5 and 15 µg, suitably between 6 and 14 µg, for example between 7 and 13 µg or between 8 and 12 µg or between 9 and 11 µg, or 10 µg. In a further embodiment, the human dose of the immunogenic composition comprises 3D-MPL at a level of about 5 µg, for example between 1 and 9 µg, or between 2 and 8 µg or suitably between 3 and 7 µg or 4 and µg, or 5 µg.

In other embodiments, the lipopolysaccharide can be a β(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. Nonetheless, each of these references is incorporated herein by reference. In addition to the aforementioned immunostimulants (that are similar in structure to that of LPS or MPL or 3D-MPL), acylated monosaccharide and disaccharide derivatives that are a sub-portion to the above structure of MPL are also suitable adjuvants. In other embodiments, the adjuvant is a synthetic derivative of lipid A, some of which are described as TLR-4 agonists, and include, but are not limited to: OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026); OM 294 DP (3S, 9 R)-3-[(R)-dodecanoyloxytetradecanoylamino]-4-oxo-5-aza-9(R)-[(R)-3-hydroxytetradecanoylamino]decan-1,10-diol, 1,10-bis(dihydrogenophosphate) (WO 99/64301 and WO 00/0462); and OM 197 MP-Ac DP (3S-, 9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate)(WO 01/46127).

Other TLR4 ligands which can be used are alkyl Glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signaling response through TLR-4 (Sabroe et al, JI 2003 p1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, and muramyl dipeptide (MDP). In one embodiment the TLR agonist is HSP 60, 70 or 90. Other suitable TLR-4 ligands are as described in WO 2003/011223 and in WO 2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. For example, one suitable TLR-4 ligand is ER804057.

Additional TLR agonists are also useful as adjuvants. The term "TLR agonist" refers to an agent that is capable of causing a signaling response through a TLR signaling pathway, either as a direct ligand or indirectly through generation of endogenous or exogenous ligand. Such natural or synthetic TLR agonists can be used as alternative or additional adjuvants. A brief review of the role of TLRs as adjuvant receptors is provided in Kaisho & Akira, *Biochimica et Biophysica Acta* 1589:1-13, 2002. These potential adjuvants include, but are not limited to agonists for TLR2, TLR3, TLR7, TLR8 and TLR9. Accordingly, in one embodiment, the adjuvant and immunogenic composition further comprises an adjuvant which is selected from the group consisting of: a TLR-1 agonist, a TLR-2 agonist, TLR-3 agonist, a TLR-4 agonist, a TLR-5 agonist, a TLR-6 agonist, TLR-7 agonist, a TLR-8 agonist, TLR-9 agonist, or a combination thereof.

In one embodiment of the present invention, a TLR agonist is used that is capable of causing a signaling response through TLR-1. Suitably, the TLR agonist capable of causing a signaling response through TLR-1 is selected from: Tri-acylated lipopeptides (LPs); phenol-soluble modulin; Mycobacterium tuberculosis LP; S-(2,3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorferi*.

In an alternative embodiment, a TLR agonist is used that is capable of causing a signaling response through TLR-2. Suitably, the TLR agonist capable of causing a signaling response through TLR-2 is one or more of a lipoprotein, a peptidoglycan, a bacterial lipopeptide from *M tuberculosis, B burgdorferi* or *T pallidum;* peptidoglycans from species including *Staphylococcus aureus;* lipoteichoic acids, mannuronic acids, Neisseria porins, bacterial fimbriae, Yersina virulence factors, CMV virions, measles haemagglutinin, and zymosan from yeast.

In an alternative embodiment, a TLR agonist is used that is capable of causing a signaling response through TLR-3. Suitably, the TLR agonist capable of causing a signaling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signaling response through TLR-5. Suitably, the TLR agonist capable of causing a signaling response through TLR-5 is bacterial flagellin.

In an alternative embodiment, a TLR agonist is used that is capable of causing a signaling response through TLR-6. Suitably, the TLR agonist capable of causing a signaling response through TLR-6 is mycobacterial lipoprotein, di-acylated LP, and phenol-soluble modulin. Additional TLR6 agonists are described in WO 2003/043572.

In an alternative embodiment, a TLR agonist is used that is capable of causing a signaling response through TLR-7. Suitably, the TLR agonist capable of causing a signaling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO 2002/085905.

In an alternative embodiment, a TLR agonist is used that is capable of causing a signaling response through TLR-8. Suitably, the TLR agonist capable of causing a signaling response through TLR-8 is a single stranded RNA (ssRNA), an imidazoquinoline molecule with anti-viral activity, for example resiquimod (R848); resiquimod is also capable of recognition by TLR-7. Other TLR-8 agonists which can be used include those described in WO 2004/071459.

In an alternative embodiment, a TLR agonist is used that is capable of causing a signaling response through TLR-9. In one embodiment, the TLR agonist capable of causing a signaling response through TLR-9 is HSP90. Alternatively, the TLR agonist capable of causing a signaling response through TLR-9 is bacterial or viral DNA, DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the immunogenic compositions of the present invention are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides of the present invention are typically deoxynucleotides. In a specific embodiment the internucleotide in the oligonucleotide is phosphorodithioate, or suitably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. Nos. 5,666,153, 5,278,302 and WO 95/26204.

Other adjuvants that can be used in immunogenic compositions with a PreF antigens, e.g., on their own or in combination with 3D-MPL, or another adjuvant described herein, are saponins, such as QS21.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria* Molina), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1, which are incorporated herein by reference. Other saponins which have been used in systemic vaccination studies include those derived from other plant species such as *Gypsophila* and *Saponaria* (Bomford et al., Vaccine, 10(9): 572-577, 1992).

QS21 is an Hplc purified non-toxic fraction derived from the bark of *Quillaja Saponaria* Molina. A method for producing QS21 is disclosed in U.S. Pat. No. 5,057,540. Non-reactogenic adjuvant formulations containing QS21 are described in WO 96/33739. The aforementioned references are incorporated by reference herein. Said immunologically active saponin, such as QS21, can be used in amounts of between 1 and 50 µg, per human dose of the immunogenic composition. Advantageously QS21 is used at a level of about 25 µg, for example between 20-30 µg, suitably between 21-29 µg or between 22-28 µg or between 23-27 µg or between 24-26 µg, or 25 µg. In another embodiment, the human dose of the immunogenic composition comprises QS21 at a level of about 10 µg, for example between 5 and 15 µg, suitably between 6-14 µg, for example between 7-13 µg or between 8-12 µg or between 9-11 µg, or 10 µg. In a further embodiment, the human dose of the immunogenic composition comprises QS21 at a level of about 5 µg, for example between 1-9 µg, or between 2-8 µg or suitably between 3-7 µg or 4-6 µg, or 5 µg. Such formulations comprising QS21 and cholesterol have been shown to be successful Th1 stimulating adjuvants when formulated together with an antigen. Thus, for example, PreF polypeptides can favorably be employed in immunogenic compositions with an adjuvant comprising a combination of QS21 and cholesterol.

Optionally, the adjuvant can also include mineral salts such as an aluminium or calcium salts, in particular aluminium hydroxide, aluminium phosphate and calcium phosphate. For example, an adjuvant containing 3D-MPL in combination with an aluminium salt (e.g., aluminium hydroxide or "alum") is suitable for formulation in an immunogenic composition containing a PreF antigen for administration to a human subject.

Another class of suitable Th1 biasing adjuvants for use in formulations with PreF antigens includes OMP-based immunostimulatory compositions. OMP-based immunostimulatory compositions are particularly suitable as mucosal adjuvants, e.g., for intranasal administration. OMP-based immunostimulatory compositions are a genus of preparations of outer membrane proteins (OMPs, including some porins) from Gram-negative bacteria, such as, but not limited to, *Neisseria* species (see, e.g., Lowell et al., J. Exp. Med. 167: 658, 1988; Lowell et al., Science 240:800, 1988; Lynch et al., Biophys. J. 45:104, 1984; Lowell, in "New Generation Vaccines" 2nd ed., Marcel Dekker, Inc., New York, Basil, Hong Kong, page 193, 1997; U.S. Pat. No. 5,726,292; U.S. Pat. No. 4,707,543), which are useful as a carrier or in compositions for immunogens, such as bacterial or viral antigens. Some OMP-based immunostimulatory compositions can be referred to as "Proteosomes," which are hydrophobic and safe for human use. Proteosomes have the capability to auto-assemble into vesicle or vesicle-like OMP clusters of about 20 nm to about 800 nm, and to noncovalently incorporate, coordinate, associate (e.g., electrostatically or hydrophobically), or otherwise cooperate with protein antigens (Ags), particularly antigens that have a hydrophobic moiety. Any preparation method that results in the outer membrane protein component in vesicular or vesicle-like form, including multi-molecular membranous structures or molten globular-like OMP compositions of one or more OMPs, is included within the definition of Proteosome. Proteosomes can be prepared, for example, as described in the art (see, e.g., U.S. Pat. No. 5,726,292 or U.S. Pat. No. 5,985,284). Proteosomes can also contain an endogenous lipopolysaccharide or lipooligosaccharide (LPS or LOS, respectively) originating from the bacteria used to produce the OMP porins (e.g., *Neisseria* species), which generally will be less than 2% of the total OMP preparation.

Proteosomes are composed primarily of chemically extracted outer membrane proteins (OMPs) from *Neisseria menigitidis* (mostly porins A and B as well as class 4 OMP), maintained in solution by detergent (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206). Proteosomes can be formulated with a variety of antigens such as purified or recombinant proteins derived from viral sources, including the PreF polypeptides disclosed herein, e.g., by diafiltration or traditional dialysis processes. The gradual removal of detergent allows the formation of particulate hydrophobic complexes of approximately 100-200 nm in diameter (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206).

"Proteosome: LPS or Protollin" as used herein refers to preparations of proteosomes admixed, e.g., by the exogenous addition, with at least one kind of lipopolysaccharide to provide an OMP-LPS composition (which can function as an immunostimulatory composition). Thus, the OMP-LPS composition can be comprised of two of the basic components of Protollin, which include (1) an outer membrane protein preparation of Proteosomes (e.g., Projuvant) prepared from Gram-negative bacteria, such as *Neisseria meningitidis*, and (2) a preparation of one or more liposaccharides. A lipooligosaccharide can be endogenous (e.g., naturally contained with the OMP Proteosome preparation), can be admixed or combined with an OMP preparation from an exogenously prepared lipo-oligosaccharide (e.g., prepared from a different culture or microorganism than the OMP preparation), or can be a combination thereof. Such exogenously added LPS can be from the same Gram-negative bacterium from which the OMP preparation was made or from a different Gram-negative bacterium. Protollin should also be understood to optionally include lipids, glycolipids, glycoproteins, small molecules, or the like, and combinations thereof. The Protollin can be prepared, for example, as described in U.S. Patent Application Publication No. 2003/0044425.

Combinations of different adjuvants, such as those mentioned hereinabove, can also be used in compositions with PreF antigens. For example, as already noted, QS21 can be formulated together with 3D-MPL. The ratio of QS21:3D-MPL will typically be in the order of 1:10 to 10:1; such as 1:5 to 5:1, and often substantially 1:1. Typically, the ratio is in the range of 2.5:1 to 1:1 3D-MPL: QS21. Another combination adjuvant formulation includes 3D-MPL and an aluminium salt, such as aluminium hydroxide. When formulated in combination, this combination can enhance an antigen-specific Th1 immune response.

In some instances, the adjuvant formulation includes an oil-in-water emulsion, or a mineral salt such as a calcium or aluminium salt, for example calcium phosphate, aluminium phosphate or aluminium hydroxide.

One example of an oil-in-water emulsion comprises a metabolisable oil, such as squalene, a tocol such as a tocopherol, e.g., alpha-tocopherol, and a surfactant, such as polysorbate 80 or Tween 80, in an aqueous carrier, and does not contain any additional immunostimulants(s), in particular it does not contain a non-toxic lipid A derivative (such as 3D-MPL) or a saponin (such as QS21). The aqueous carrier can be, for example, phosphate buffered saline. Additionally the oil-in-water emulsion can contain span 85 and/or lecithin and/or tricaprylin.

In another embodiment of the invention there is provided a vaccine composition comprising an antigen or antigen composition and an adjuvant composition comprising an oil-in-water emulsion and optionally one or more further immunostimulants, wherein said oil-in-water emulsion comprises 0.5-10 mg metabolisable oil (suitably squalene), 0.5-11 mg tocol (suitably a tocopherol, such as alpha-tocopherol) and 0.4-4 mg emulsifying agent.

In one specific embodiment, the adjuvant formulation includes 3D-MPL prepared in the form of an emulsion, such as an oil-in-water emulsion. In some cases, the emulsion has a small particle size of less than 0.2 µm in diameter, as disclosed in WO 94/21292. For example, the particles of 3D-MPL can be small enough to be sterile filtered through a 0.22 micron membrane (as described in European Patent number 0 689 454). Alternatively, the 3D-MPL can be prepared in a liposomal formulation. Optionally, the adjuvant containing 3D-MPL (or a derivative thereof) also includes an additional immunostimulatory component.

For example, when an immunogenic composition with a PreF polypeptide antigen is formulated for administration to an infant, the dosage of adjuvant is determined to be effective and relatively non-reactogenic in an infant subject. Generally, the dosage of adjuvant in an infant formulation is lower than that used in formulations designed for administration to adult (e.g., adults aged 65 or older). For example, the amount of 3D-MPL is typically in the range of 1 µg-200 µg, such as 10-100 µg, or 10 µg-50 µg per dose. An infant dose is typically at the lower end of this range, e.g., from about 1 µg to about 50 µg, such as from about 2 µg, or about 5 µg, or about 10 µg, to about 25 µg, or to about 50 µg. Typically, where QS21 is used in the formulation, the ranges are comparable (and according to the ratios indicated above). For adult and elderly populations, the formulations typically include more of an adjuvant component than is typically found in an infant formulation. In particular formulations using an oil-in-water emulsion, such an emulsion can include additional components, for example, such as cholesterol, squalene, alpha tocopherol, and/or a detergent, such as tween 80 or span85. In exemplary formulations, such components can be present in the following amounts: from about 1-50 mg cholesterol, from 2 to 10% squalene, from 2 to 10% alpha tocopherol and from 0.3 to 3% tween 80. Typically, the ratio of squalene: alpha tocopherol is equal to or less than 1 as this provides a more stable emulsion. In some cases, the formulation can also contain a stabilizer.

Where alum is present, e.g., in combination with 3D-MPL, the amount is typically between about 100 μg and 1 mg, such as from about 100 μg, or about 200 μg to about 750 μg, such as from about 500 μg per dose.

An immunogenic composition typically contains an immunoprotective quantity (or a fractional dose thereof) of the antigen and can be prepared by conventional techniques. Preparation of immunogenic compositions, including those for administration to human subjects, is generally described in Pharmaceutical Biotechnology, Vol. 61 Vaccine Design-the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Typically, the amount of protein in each dose of the immunogenic composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg. The amount utilized in an immunogenic composition is selected based on the subject population (e.g., infant or elderly). An optimal amount for a particular composition can be ascertained by standard studies involving observation of antibody titres and other responses in subjects. Following an initial vaccination, subjects can receive a boost in about 4 weeks.

It should be noted that regardless of the adjuvant selected, the concentration in the final formulation is calculated to be safe and effective in the target population. For example, immunogenic compositions for eliciting an immune response against RSV in humans are favorably administered to infants (e.g., infants between birth and 1 year, such as between 0 and 6 months, at the age of initial dose). Immunogenic compositions for eliciting an immune response against RSV are also favorably administered to elderly humans (e.g., alone or in a combination with antigens of other pathogens associated with COPD). It will be appreciated that the choice of adjuvant can be different in these different applications, and the optimal adjuvant and concentration for each situation can be determined empirically by those of skill in the art.

In certain embodiments, the immunogenic compositions are vaccines that reduce or prevent infection with RSV. In some embodiments, the immunogenic compositions are vaccines that reduce or prevent a pathological response following infection with RSV. Optionally, the immunogenic compositions containing a PreF antigen are formulated with at least one additional antigen of a pathogenic organism other than RSV. For example, the pathogenic organism can be a pathogen of the respiratory tract (such as a virus or bacterium that causes a respiratory infection). In certain cases, the immunogenic composition contains an antigen derived from a pathogenic virus other than RSV, such as a virus that causes an infection of the respiratory tract, such as influenza or parainfluenza. In other embodiments, the additional antigens are selected to facilitate administration or reduce the number of inoculations required to protect a subject against a plurality of infectious organisms. For example, the antigen can be derived from any one or more of influenza, hepatitis B, diphtheria, tetanus, pertussis, Hemophilus influenza, poliovirus, *Streptococcus* or *Pneumococcus*, among others.

Accordingly, the use of PreF antigens or nucleic acids that encode them in the preparation of a medicament for treating (either therapeutically following or prophylactically prior to) exposure to or infection by RSV is also a feature of this disclosure. Likewise, methods for eliciting an immune response against RSV in a subject are a feature of this disclosure. Such methods include administering an immunologically effective amount of a composition comprising a PreF antigen to a subject, such as a human subject. Commonly, the composition includes an adjuvant that elicits a Th1 biased immune response. The composition is formulated to elicit an immune response specific for RSV without enhancing viral disease following contact with RSV. That is, the composition is formulated to and results in a Th1 biased immune response that reduces or prevents infection with a RSV and/or reduces or prevents a pathological response following infection with a RSV. Although the composition can be administered by a variety of different routes, most commonly, the immunogenic compositions are delivered by an intramuscular or intranasal route of administration.

An immunogenic composition typically contains an immunoprotective quantity (or a fractional dose thereof) of the antigen and can be prepared by conventional techniques. Preparation of immunogenic compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Typically, the amount of protein in each dose of the immunogenic composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 1 1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg. The amount utilized in an immunogenic composition is selected based on the subject population (e.g., infant or elderly). An optimal amount for a particular composition can be ascertained by standard studies involving observation of antibody titres and other responses in subjects. Following an initial vaccination, subjects can receive a boost in about 4-12 weeks. For example, when administering an immunogenic composition containing a PreF antigen to an infant subject, the initial and subsequent inoculations can be administered to coincide with other vaccines administered during this period.

The following examples are provided to illustrate certain particular features and/or embodiments. These examples should not be construed to limit the invention to the particular features or embodiments described.

EXAMPLES

Example 1

Exemplary PreF Antigens

The PreF antigen was modified as compared to a native RSV F protein in order to stabilize the protein in its prefusion conformation, based on the prediction that an immune response generated to the prefusion conformation of F would preferentially include antibodies that would prevent binding, conformation shifting and/or other events involved in membrane fusion, thereby increasing the efficacy of the protective response.

FIGS. 1A and B schematically illustrate features of RSV F0 and exemplary PreF recombinant antigens. FIG. 1A is a representation of the RSV F0 protein. F0 is a pre-protein consisting of 574 amino acids. The F0 pre-protein is proteolytically processed and glycosylated following translation. A signal peptide, which is later removed by a signal peptidase, targets translation of the F0 pre-protein to the reticulum endoplasmic (RE). Nascent peptide in the RE is then N-glycosylated at multiple sites (represented by triangles). Furin cleavage of F0 generates F2 and F1 peptide domains, which are folded and assembled together as a trimer of F2-F1 heterodimers (that is, 3 times F2-F1). In its native state, the F protein is anchored to the membrane by a transmembrane helix in the C-terminal region. Additional features of the F0 polypeptide include, 15 Cysteine residues, 4 characterized neutralizing epitopes, 2 coiled-coil regions, and a lipidation motif. FIG. 1B illustrates features of exemplary PreF antigens. To construct the PreF antigen, the F0 polypeptide was modified to stabilize the prefusion conformation of the F protein, thereby retaining the predominant immunogenic epitopes of the F protein as presented by the RSV virus prior to binding to and fusion with host cells. The following stabilizing mutations were introduced into the PreF antigen relative to the F0 polypeptide. First, a stabilizing coiled-coil domain was placed at the C-terminal end of the extracellular domain of the F0 polypeptide, replacing the membrane anchoring domain of F0. Second, the pep27 peptide (situated between the F2 and F1 domains in the native protein) was removed. Third, both furin motifs were eliminated. In alternative embodiments (designated PreF_V1 and PreF_V2), an immunologically active portion (e.g., amino acids 149-229) of the RSV G protein was added to the C-terminal domain.

Example 2

Production and Purification of PreF Recombinant Protein from CHO Cells.

A recombinant polynucleotide sequence encoding an exemplary PreF antigen was introduced into host CHO cells for the production of PreF antigen. Transiently transfected host cells or expanded stable populations comprising the introduced polynucleotide sequence were grown in medium and under conditions suitable for growth at an acceptable scale for the desired purpose (e.g., as generally described in Freshney (1994) *Culture of Animal Cells, a Manual of Basic Technique*, third edition, Wiley-Liss, New York and the references cited therein). Typically, the cells were grown in serum-free medium in shake flasks at 37° C. with 5% $CO_2$ and passaged at 2-3 day intervals, or in bioreactors at 29° C. with pO2 maintained at 20%.

To recover recombinant PreF antigen, the cell culture was centrifuged and the cell culture supernatant stored at 80° C. until further use. For further analysis, two liter aliquots of cell culture supernatant were diluted 2× with purified water and adjusted to pH 9.5 with NaOH. The supernatant was loaded at a rate of 14 ml/min. onto a Q Sepharose FF ion exchange column (60 ml, 11.3 cm), equilibrated in 20 mM piperazine pH 9.5. After washing the column with the starting buffer, elution was performed with a NaCl gradient from 0 to 0.5 M NaCl in 20 column volumes (fraction size 10 ml). Fractions were analyzed on SDS PAGE gel by silver staining and western blot. Fractions containing substantial PreF protein were then pooled prior to further processing.

The pooled elution of the Q step (~130 mls) was subjected to buffer exchange into 10 mM phosphate, pH 7.0 using the bench-scale TFF system from Millipore with the Pelllicon XL PES Biomax 100 (MWCO 10,000 Da) membrane cassette. The resulting material had a pH of 7.0 and a conductivity of 1.8 mS/cm. 100 ml of this sample was loaded at 5 ml/min. on a 10 ml Hydroxy apatite Type II (HA TII) gel (XK 16, height=5 cm) equilibrated with 10 mM $PO_4$ (Na) buffer pH 7.0. After washing the column with the starting buffer, elution was performed with a gradient from 10 mM to 200 mM PO4 (Na) pH 7.0 in 20 column volumes. Fractions were again analysed on SDS PAGE with silver staining and coomassie blue, and the positive fractions were pooled.

Following affinity chromatography, the pooled fractions were concentrated and the buffer exchanged into DPBS (pH ~7.4) using a Vivaspin 20 concentrator unit, 10,000 Da MWCO. The final product was about 13 ml. Protein concentration was 195 µg/ml, assessed by Lowry assay. Purity was greater than 95%. This purified PreF antigen preparation was filter sterilized and stored at −20° C. prior to use.

Example 3

Characterization of the PreF Recombinant Protein Produced in CHO Cells.

PreF recombinant protein produced in CHO cells was characterized by asymmetrical field flow fractionation (AFF-MALS) and compared to a chimeric antigen including RSV F and G protein components. AFF-MALS allows separation of protein species according to their molecular size in a liquid flow with minimal matrix interaction and further analysis by multi-angle light scattering for accurate molecular weight determination. FIG. 2A shows that more than 65% of purified FG material is found as high molecular weight oligomers (1000-100 000 KDa) in is final PBS buffer while 3% remain in monomeric form.

FIG. 2B shows that the purified PreF protein is folded in his trimeric form to a proportion of 73% in PBS buffer. 10% of the material is found as 1000 to 20 000 KDa oligomers. These results indicate that the recombinant PreF protein expressed in CHO cells is folded as a trimer as predicted for the native state.

Purified PreF protein was also crosslinked with glutaraldehyde for the double purpose of confirming the soluble nature of the protein in phosphate buffer solution and of generating aggregates for comparative in vivo evaluation with FG protein (see Example 7 below). Glutaraldehyde crosslinking is known for providing a good assessment of the quaternary structure of a protein, and is described in (*Biochemistry*, 36:10230-10239 (1997); *Eur. Biochem.*, 271:4284-4292 (2004)).

Protein was incubated with 1%, 2% and 5% of glutaraldehyde crosslinking agent for four hours at 4° C. and the reaction was blocked by addition of $NaBH_4$. Excess glutaraldehyde was removed by column desalting in PBS buffer.

Resulting protein was quantified by absorbance at 280 nm and evaluated by SDS PAGE in denaturing and reducing condition. The majority of purified recombinant PreF was determined to migrate as a trimer in PBS solution. Increasing the incubation temperature to 23° C. was required to convert majority of trimeric protein to high molecular weight aggregates, as confirmed by SDS PAGE.

Example 4

In Vitro Neutralization Inhibition by the PreF Antigen

Human sera obtained from volunteers were screened for reactivity against RSV A by ELISA and used in the neutralization inhibition (NI) assay at relevant dilution based on prior RSV neutralization potential titration established for each serum sample. Briefly, Sera were mixed with inhibitor proteins (PreF or a control protein corresponding essentially to the chimeric FG disclosed in U.S. Pat. No. 5,194,595, designated RixFG) at concentrations of 25 µg/ml in DMEM with 50% 199-H medium, with 0.5% FBS, 2 mM glutamine, 50 µg/ml genamycin (all Invitrogen), and incubated 1.5 to 2 hours at 37° C. on a rotating wheel. 20 µl the serial dilutions of sera and proteins were mixed in a round bottom 96-well plate with a RSV A titred to optimize the range of inhibition for each serum sample. The resulting mixtures were incubated for 20 minutes at 33° C. under 5% CO2 to maintain pH.

The sera-inhibitor-virus mixtures were then placed into previously Vero cell-seeded flat bottom 96-well plates and incubated for 2 hours at 33° C. prior to addition of 160 µl of medium. The plates were further incubated for 5-6 days at 33° C. with 5% CO2 until immunofluorescence assay for NI titer detection. Following fixation for 1 hour with 1% paraformaldehyde in phosphate buffered saline (PBS), plates were blocked with 2% milk/PBS and Block biffer. Goat anti-RSV antibody (Biodesign Internation; 1:400) was added to each well without rinsing and incubated for 2 hours at room temperature (RT). Samples were washed 2× with PBS and anti-goat IgG-FITC (Sigma; 1:400) in blocking buffer was added to the wells. The plates were again incubated for 2 hours at RT and washed 2× as above prior to reading. A well was considered positive when ≥1 fluorescent syncytium was detected. The 50% tissue culture infective dose (TCID50) calculations were performed using the Spearman-Karber (SK) method and percentages of NI calculated as follow: [(Neut titer of 0 µg/ml inhibitor−Neut titer of 25 µg/ml inhibitor)/Neut titer of 0 µg/ml inhibitor]×100. Exemplary results shown in FIG. 3 indicate that PreF is superior to FG in NI in 16/21 donors tested.

Example 5

PreF Antigen is Immunogenic

To demonstrate immunogenicity of the PreF antigen, mice were immunized twice IM at two weeks interval with preF (6.5, 3.1, 0.63, 0.13, and 0.025 µg/ml) and a Th1 adjuvant containing 3D MPL and QS21 at 1/20 of human dose ("ASO1E") or preF (1, 0.2 and 0.04 µg/ml) and a Th1 adjuvant containing 3D MPL and alum 1/10 of human dose ("AS04C") and serum was collected three weeks later.

Antigen-specific IgG antibody titers were determined on pooled serum samples by ELISA according to standard procedures. Briefly, 96-well plates were coated with purified inactivated RSV A, RSV B and homologous preF protein and incubated overnight at 4° C. Serum samples were serially diluted in blocking buffer starting at an initial concentration of 1:50, along with purified mouse IgG Sigma, ON) at starting concentrations of 200 ng/ml and incubated for 2 h at room temperature. Bound antibody was detected with horseradish peroxidase (HRP)-conjugated anti-mouse IgG (Sigma, ON). 3,3A,5,5A-tetramethylbenzidine (TMB, BD Opt EIATM, BD Biosciences, ON) was used as the substrate for HRP. 50 µl of 1M H2SO4 was added to each well to stop the reaction. Absorbance values for each well were detected at 450 nm with a Molecular Devices microplate reader (Molecular Devices, USA).

Representative results detailed in FIGS. 4A and 4B show that strong titers are elicited against both RSV A and RSV B following immunization with preF antigen.

Example 6

PreF Elicits Neutralizing Antibodies

The presence and quantity of neutralizing antibodies was assessed in serum samples of mice immunized as described above in Example 5. Pooled sera from immunized animals were serially diluted from a starting dilution of 1:8 in RSV medium in 96-well plates (20 µl/well). Control wells contained RSV medium only, or goat anti-RSV antibody at 1:50 (Biodesign international). 500-1000 infectious doses of a representative RSV A or B strain were added to the wells, and the plates were incubated for 20 minutes at 33° C., 5% $CO_2$, before the mixture was transferred to 96-well flat-bottomed plates previously seeded with $1 \times 10^5$ cells/mL Vero cells. Cells were incubated for approximately 2 hours at 33° C., 5% $CO_2$ and refed, prior to incubation for 5-6 days at the same temperature. Supernatants were removed; plates were washed with PBS and adhering cells fixed with 1% paraformaldehyde in PBS for 1 hour, followed by indirect immunofluorescence (IFA) using a goat anti RSV primary antibody and anti-goat IgG-FITC for detection.

Representative results shown in FIGS. 5A and 5B, respectively, demonstrate that significant neutralizing antibodies against both RSV strains are detected in sera of animals immunized with preF.

Example 7

PreF Protects Against RSV Challenge

Mice were immunized twice IM at a two week interval as described above, and challenged three weeks after the second injection with RSV A. Protection against RSV was evaluated by measuring the virus present in lungs following challenge. In brief, lungs from immunized animals were aseptically removed following euthanasia and washed in RSV medium using 2 volumes of 10 ml/lung in 15 ml tubes. Lungs were then weighed and homogenized individually in RSV medium with an automated Potter homogenizer (Fisher, Nepean ON), and centrifuged at 2655×g for 2 minutes at 4° C. The virus present in the supernatants was titered by serial dilution (eight replicates starting at 1:10) on a previously seeded Vero cell (ATCC# CCL-81) monolayer in 96-well plates and incubated for 6 days. RSV was detected by indirect IFA following fixing in 1% paraformaldehyde/PBS pH7.2, with goat anti-RSV primary antibody and FITC labeled anti-goat IgG secondary antibody.

Figure 6B:
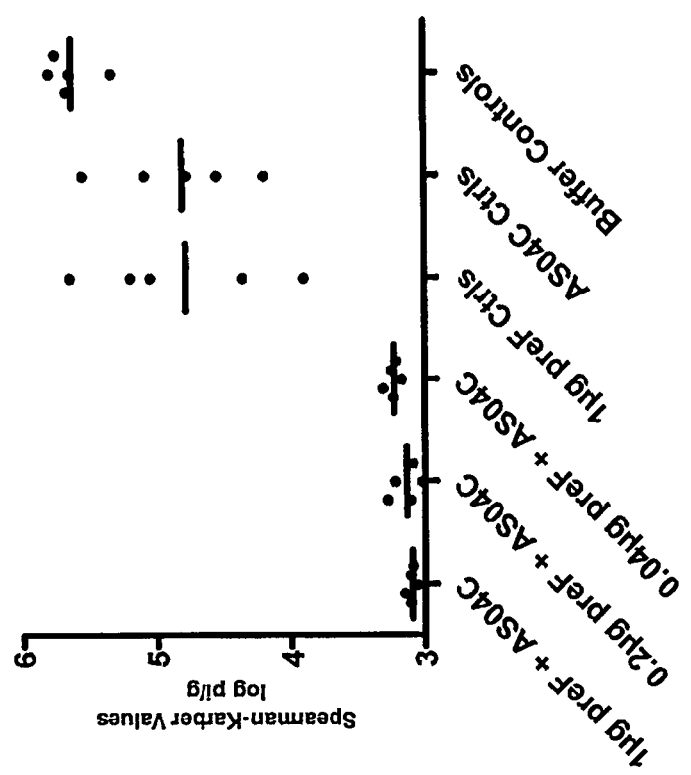
FIGS. 6A and B are graphs indicating protection against challenge provided by the RSV PreF antigen in mice.

Representative results shown in FIGS. 6A and B demonsrate that doses equal to or higher than 0.04 µg when given in presence of adjuvant elicit strong protection against RSV.

Example 8

PreF does not Induce Pulmonary Eosinophil Recruitment Following Challenge

To assess the potential of the PreF antigen to provoke exacerbated disease following immunization and subsequent challenge, groups of mice (5 mice/group) were immunized twice each with (a) 10 μg gluteraldehyde-treated preF, (b) 10 μg preF or (c) 10 μg FG without adjuvant. Mice were challenged with RSV A 3 weeks post-boost and bronchoalveolar lavage (BAL) was performed 4 days post challenge. Total leukocyte infiltrates in BAL were enumerated per mouse as well as differential enumerations (300 cells) based on cell morphology of macrophages/monocytes, neutrophils, eosinophils and lymphocytes.

Figure 7:
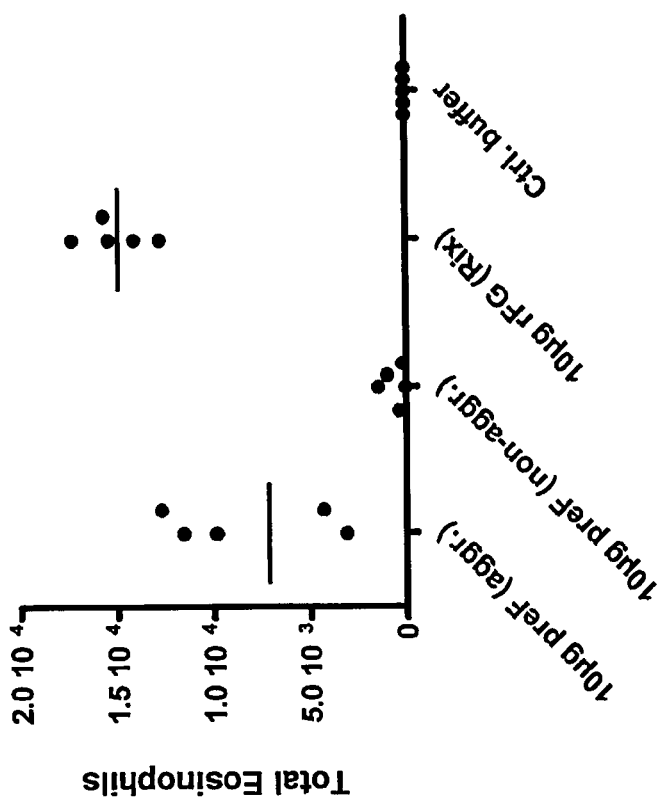
FIG. 7 is a graph evaluating BAL leukocytes following immunization and challenge.

Total cell numbers were multiplied by differential percentages of eosinophils for each animal. Represented are geometric means per group with 95% confidence limits. Representative results shown in FIG. 7 demonstrate that eosinophils are not recruited to the lungs following immunization with preF and challenge. Furthermore, these results suggest that the soluble nature of the preF antigen, as compared to a deliberately aggregated form of preF (gluteraldehyde treatment) or FG antigen (naturally aggregated) does not favour eosinophils.

Sequence Listing

SEQ ID NO: 1
Nucleotide sequence encoding RSV reference Fusion protein Strain A2 GenBank Accession No. U50362

```
atggagttgctaatcctcaaagcaaatgcaattaccacaatcctcactg
cagtcacatttgttttgcttctggtcaaaacatcactgaagaatttat
caatcaacatgcagtgcagtagcaaaggctatcttagtgctctgagaac
tggttggtataccagtgttataactatagattaagtaatatcaaggaaa
ataagtgtaatggaacagatgctaaggtaaaattgataaacaagaatta
gataaatataaaaatgctgtaacagaattgcagttgctcatgcaaagca
cccagcaacaaacaatcgagccagaagagaactaccaaggtttatgaat
tatacactcaaaatgccaaaaaaccaatgtaacattaagcaagaaaag
gaaaagaagatttcttggttttgttaggtgttggatctgcaatcgcca
gtggcgttgctgtatctaaggtcctgcacctgaaggggaagtgaacaag
atcaaaagtgctctactatccacaaacaaggctgtagtcagttatcaaa
tggagttagtgtcttaaccagcaaagtgttagacctcaaaaactatata
gaaaacaattgttacctattgtgaacaagcaaagctgcagcatatcaaa
tatagcaactgtatagagttccaacaaaagaacaacagactactagaga
ttaccagggaatttagtgttaagcaggtgtaactacacctgtaagcact
tacatgttaactaatagtgaattattgtcattatcaatgatatgcctat
aacaaatgatcagaaaagttaatgtccaacaatgttcaaatgttagac
agcaaagttactctatcatgtccataataaaagaggaagtcttagcata
tgtgtacaattaccactatatggtgttatagatacacctgttggaaac
tacacacatcccctatgtacaaccaacacaaaagaagggtccaacatc
tgtttaacaagaactgacagaggtggtactgtgacaatgcaggatcagt
atctttcttcccacaagctgaaacatgtaaagtcaatcaaatcgagtat
tttgtgacacaatgaacagtttaacattaccaagtgaagtaaactctgc
aatgttgacatattcaaccccaaatatgattgtaaaattatgacttcaa
aaacgatgtaagcagctccgttatcacatctctaggagccattgtgtca
tgctatggcaaaacaaatgtacagcatccaataaaaatcgtggaatcat
aaagacattttctaacgggtgcgatatgtatcaaataaaggggtggaca
ctgtgtctgtaggtaacacattatattatgtaaaaagcaagaaggtaaa
agtctctatgtaaaaggtgaaccaataataaatttctatgacccttagt
attccctctgatgaatttgatgcatcaatatctcaagtcaacgagaag
attaacagagcctagcatttattcgtaaatccgatgaattattacataa
tgtaaatgctggtaatccaccataaatatcatgataactactataatta
tagtgattatagtaatattgttatcttaattgctgttggactgctctta
tactgtaaggccagaagcacaccagtcacactaagaaagatcaactgag
tggtataaataatattgcatttagtaactaa
```

SEQ ID NO: 2
Amino acid sequence of RSV reference F protein precursor F0 Strain A2 GenBank Accession No. AAB86664

MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYID
KQLLPIVNKQSCSISNIATVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
KDVSSSVITSLGAIVSCYGKTKCTASNKNRGIITFSNGCDYVSNKGVDTV
SVGNTLYYVNKQEGKSLYVKGEPIINFYDPLVEPSDEFDASISQVNEKIN
QSLAFIRKSDELLHNVNAGKSTINIMITTIIIVIIVILLSLIAVGLLLYC
KARSTPVTLSKDQLSGINNIAFSN

SEQ ID NO: 3
Nucleotide sequence encoding RSV reference G protein Strain Long

```
Atgtccaaaaacaaggaccaacgcaccgctaagacactagaaaagacctg
ggacactctcaatcatttattattcatatcatcgggcttatataagttaa
atcttaaatctatagcacaaatcacattatccattctggcaatgataatc
tcaacttcacttataattacagccatcatattcatagcctcggcaaacca
caaagtcacactaacaactgcaatcatacaagatgcaacaagccagatca
agaacacaaccccaacatacctcactcaggatcctcagcttggaatcagc
ttctccaatctgtctgaaattacatcacaaaccaccaccatactagcttc
aacaacaccaggagtcaagtcaaacctgcaacccacaacagtcaagacta
aaaacacaacaacaacccaaacacaacccagcaagcccactacaaaacaa
cgccaaaacaaaccaccaaacaaacccaataatgattttcacttcgaagt
gtttaactttgtaccctgcagcatatgcagcaacaatccaacctgctggg
ctatctgcaaaagaataccaaacaaaaaaccaggaaagaaaaccaccacc
```

-continued aagcctacaaaaaaaccaaccttcaagacaaccaaaaaagatctcaaacc tcaaaccactaaaccaaaggaagtacccaccaccaagcccacagaagagc caaccatcaacaccaccaaaacaaacatcacaactacactgctcaccaac aacaccacaggaaatccaaaactcacaagtcaaatggaaaccttccactc aacctcctccgaaggcaatctaagcccttctcaagtctccacaacatccg agcacccatcacaaccctcatctccacccaacacaacacgccagtag SEQ ID NO: 4
Amino acid sequence of RSV reference G protein
MSKNKDQRTAKTLEKTWDTLNHLLFISSGLYKLNLKSIAQITLSILAMII

STSLIITAIIFIASANHKVTLTTAIIQDATSQIKNTTPTYLTQDPQLGIS

FSNLSEITSQTTTILASTTPGVKSNLQPTTVKTKNTTTTQTQPSKPTTKQ

RQNKPPNKPNNDFHFEVFNFVPCSICSNNPTCWAICKRIPNKKPGKKTTT

KPTKKPTFKTTKKDLKPQTTKPKEVPTTKPTEEPTINTTKTNITTTLLTN

NTTGNPKLTSQMETFHSTSSEGNLSPSQVSTTSEHPSQPSSPPNTTRQ

Seq ID NO: 5
Nucleotide sequence of PreF analog optimized for CHO
aagcttgccaccatggagctgctgatcctgaaaaccaacgccatcaccgc catcctggccgccgtgaccctgtgcttcgcctcctcccagaacatcaccg aggagttctaccagtccacctgctccgccgtgtccaagggctacctgtcc gccctgcggaccggctggtacacctccgtgatcaccatcgagctgtccaa catcaaggaaaacaagtgcaacggcaccgacgccaaggtgaagctgatca agcaggagctggacaagtacaagagcgccgtgaccgaactccagctgctg atgcagtccacccctgccaccaacaacaagtttctgggcttcctgctggg cgtgggctccgccatcgcctccggcatcgccgtgagcaaggtgctgcacc tggagggcgaggtgaacaagatcaagagcgccctgctgtccaccaacaag gccgtggtgtccctgtccaacggcgtgtccgtgctgacctccaaggtgct ggatctgaagaactacatcgacaagcagctgctgcctatcgtgaacaagc agtcctgctccatctccaacatcgagaccgtgatcgagttccagcagaag aacaaccggctgctggagatcacccgcgagttctccgtgaacgccggcgt gaccacccctgtgtccacctacatgctgaccaactccgagctgctgtccc tgatcaacgacatgcctatcaccaacgaccagaaaaaactgatgtccaac aacgtgcagatcgtgcggcagcagtcctacagcatcatgagcatcatcaa ggaagaggtgctggcctacgtggtgcagctgcctctgtacggcgtgatcg acaccccttgctggaagctgcacacctcccccctgtgcaccaccaacacc aaggagggctccaacatctgcctgacccggaccgaccggggctggtactg cgacaacgccggctccgtgtccttcttccctctggccgagacctgcaagg tgcagtccaacgggtgttctgcgacaccatgaactccctgaccctgcct tccgaggtgaacctgtgcaacatcgacatcttcaaccccaagtacgactg caagatcatgaccagcaagaccgacgtgtcctccagcgtgatcacctccc tgggcgccatcgtgtcctgctacggcaagaccaagtgcaccgcctccaac aagaaccggggaatcatcaagaccttctccaacggctgcgactacgtgtc caataagggcgtggacaccgtgtccgtgggcaacacactgtactacgtga ataagcaggagggcaagagcctgtacgtgaagggcgagcctatcatcaac ttctacgaccctctggtgttcccttccgacgagttcgacgcctccatcag ccaggtgaacgagaagatcaaccagtccctggccttcatccggaagtccg acgagaagctgcataacgtggaggacaagatcgaggagatcctgtccaaa atctaccacatcgagaacgagatcgcccggatcaagaagctgatcggcga ggcctgataatctaga SEQ ID NO: 6
Amino acid sequence of PreF analog
MELLILKTNAITAILAAVTLCFASSQNITEEFYQSTCSAVSKGYLSALRT

GWYTSVITIELSNIKENKCNGTDAKVKLIKQELDKYKSAVTELQLLMQST

PATNNKFLGFLLGVGSAIASGIAVSKVLHLEGEVNKIKSALLSTNKAVVS

LSNGVSVLTSKVLDLKNYIDKQLLPIVNKQSCSISNIETVIEFQQKNNRL

LEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGS

NICLTRTDRGWYCDNAGSVSFFPLAETCKVQSNRVFCDTMNSLTLPSEVN

LCNIDIFNPKYDCKIMTSKTDVSSSVITSLGAIVSCYGKTKCTASNKNRG

IIKTFSNGCDYVSNKGVDTVSVGNTLYYVNKQEGKSLYVKGEPIINFYDP

LVFPSDEFDASISQVNEKINQSLAFIRKSDEKLHNVEDKIEEILSKIYHI

ENEIARIKKLIGEA

Seq ID NO: 7
Nucleotide sequence encoding PreF_V1 optimized for CHO
aagcttgccaccatggagctgctgatcctcaagaccaacgccatcaccgc catcctggccgccgtgaccctgtgcttcgcctcctcccagaacatcaccg aagagttctaccagtccacctgctccgccgtgtccaagggctacctgtcc gccctgcggaccggctggtacacctccgtgatcaccatcgagctgtccaa catcaaagaaaacaagtgcaacggcaccgacgccaaggtcaagctgatca agcaggaactggacaagtacaagagcgccgtgaccgaactccagctgctg atgcagtccacccctgccaccaacaacaagaagtttctgggcttcctgct gggcgtgggctccgccatcgcctccggcatcgccgtgagcaaggtgctgc acctggagggcgaggtgaacaagatcaagagcgccctgctgtccaccaac aaggccgtggtgtccctgtccaacggcgtgtccgtgctgacctccaaggt gctggatctgaagaactacatcgacaagcagctgctgcctatcgtgaaca agcagtcctgctccatctccaacatcgagaccgtgatcgagttccagcag aagaacaaccggctgctggagatcacccgcgagttctccgtgaacgccgg cgtgaccacccctgtgtccacctacatgctgacaaactccgagctgctct ccctgatcaacgacatgcctatcaccaacgaccaaaaaagctgatgtcc aacaacgtgcagatcgtgcggcagcagtcctacagcatcatgagcatcat caaggaagaagtcctggcctacgtcgtgcagctgcctctgtacggcgtga tcgacacccttgctggaagctgcacacctcccccctgtgcaccaccaac accaaagagggctccaacatctgcctgacccggaccgaccggggctggta ctgcgacaacgccggctccgtgtccttcttccctctggccgagacctgca aggtgcagtccaaccgggtgttctgcgacaccatgaactccctgaccctg -continued ccttccgaggtgaacctgtgcaacatcgacatcttcaaccccaagtacga
ctgcaagatcatgaccagcaagaccgacgtgtcctccagcgtgatcacct
ccctgggcgccatcgtgtcctgctacggcaagaccaagtgcaccgcctcc
aacaagaaccggggaatcatcaagaccttctccaacggctgcgactacgt
gtccaataagggcgtggacaccgtgtccgtgggcaacacactgtactacg
tgaataagcaggaaggcaagagcctgtacgtgaagggcgagcctatcatc
aacttctacgaccctctggtgttcccttccgacgagttcgacgcctccat
cagccaggtcaacgagaagatcaaccagtccctggccttcatccggaagt
ccgacgagaagctgcataacgtggaggacaagatcgaagagatcctgtcc
aaaatctaccacatcgagaacgagatcgcccggatcaagaagctgatcgg
cgaggctggcggctctggcggcagcggcggctccaagcagcggcagaaca
agcctcctaacaagcccaacaacgacttccacttcgaggtgttcaacttc
gtgccttgctccatctgctccaacaaccctacctgctgggccatctgcaa
gagaatccccaacaagaagcctggcaagaaaaccaccaccaagcctacca
agaagcctaccttcaagaccaccaagaaggaccacaagcctcagaccaca
aagcctaaggaagtgccaaccaccaagcaccaccaccatcaccactgata
atcta Seq ID NO: 8
PreF_V1 peptide for CHO
MELLILKTNAITAILAAVTLCFASSQNITEEFYQSTCSAVSKGYLSALRT
GWYTSVITIELSNIKENKCNGTDAKVKLIKQELDKYKSAVTELQLLMQST
PATNNKKFLGFLLGVGSAIASGIAVSKVLHLEGEVNKIKSALLSTNKAVV
SLSNGVSVLTSKVLDLKNYIDKQLLPIVNKQSCSISNIETVIEFQQKNNR
LLEITREFSVNAGVTTPVSTYMLTNSELLSLINDMPITNDQKKLMSNNVQ
IVRQQSYSIMSIIKEEVLAYVVQLPLYGVIDTPCWKLHTSPLCTTNTKEG
SNICLTRTDRGWYCDNAGSVSFFPLAETCKVQSNRVFCDTMNSLTLPSEV
NLCNIDIFNPKYDCKIMTSKTDVSSSVITSLGAIVSCYGKTKCTASNKNR
GIIKTFSNGCDYVSNKGVDTVSVGNTLYYVNKQEGKSLYVKGEPIINFYD
PLVFPSDEFDASISQVNEKINQSLAFIRKSDEKLHNVEDKIEEILSKIYH
IENEIARIKKLIGEAGGSGGSGGSKQRQNKPPNKPNNDFHFEVFNFVPCS
ICSNNPTCWAICKRIPNKKPGKKTTTKPTKKPTFKTTKKDHKPQTTKPKE
VPTTK Seq ID NO: 9
PreF_V2 for CHO
aagcttgccaccatggagctgctgatcctcaagaccaacgccatcaccgc
catcctggccgccgtgaccctgtgcttcgcctcctcccagaacatcaccg
aagagttctaccagtccacctgctccgccgtgtccaagggctacctgtcc
gccctgcgtaccggctggtacacctccgtgatcaccatcgagctgtccaa
catcaaagaaaacaagtgcaacggcaccgacgccaaggtcaagctgatca
agcaggaactggacaagtacaagagcgccgtgaccgaactccagctgctg
atgcagtccaccccctgccaccaacaacaagaagtttctgggcttcctgct gggcgtgggctccgccatcgcctccggcatcgccgtgagcaaggtgctgc
acctggagggcgaggtgaacaagatcaagagcgccctgctgtccaccaac
aaggccgtggtgtccctgtccaacggcgtgtccgtgctgacctccaaggt
gctggatctgaagaactacatcgacaagcagctgctgcctatcgtgaaca
agcagtcctgctccatctccaacatcgagaccgtgatcgagttccagcag
aagaacaaccggctgctggagatcacccgcgagttctccgtgaacgccgg
cgtgaccacccctgtgtccacctacatgctgacaaactccgagctgctct
ccctgatcaacgacatgcctatcaccaacgaccaaaaaaagctgatgtcc
aacaacgtgcagatcgtgcggcagcagtcctacagcatcatgagcatcat
caaggaagaagtcctggcctacgtcgtgcagctgcctctgtacggcgtga
tcgacacccttgctggaagctgcacacctcccccctgtgcaccaccaac
accaaagagggctccaacatctgcctgacccggaccgaccggggctggta
ctgcgacaacgccggctccgtgtccttcttccctctggccgagacctgca
aggtgcagtccaacccgggtgttctgcgacaccatgaactccctgaccctg
ccttccgaggtgaacctgtgcaacatcgacatcttcaaccccaagtacga
ctgcaagatcatgaccagcaagaccgacgtgtcctccagcgtgatcacct
ccctgggcgccatcgtgtcctgctacggcaagaccaagtgcaccgcctcc
aacaagaaccggggaatcatcaagaccttctccaacggctgcgactacgt
gtccaataagggcgtggacaccgtgtccgtgggcaacacactgtactacg
tgaataagcaggaaggcaagagcctgtacgtgaagggcgagcctatcatc
aacttctacgaccctctggtgttcccttccgacgagttcgacgcctccat
cagccaggtcaacgagaagatcaaccagtccctggccttcatccggaagt
ccgacgagaagctgcataacgtggaggacaagatcgaagagatcctgtcc
aaaatctaccacatcgagaacgagatcgcccggatcaagaagctgatcgg
cgaggctggcggcaagcagcggcagaacaagcctcctaacaagcccaaca
acgacttccacttcgaggtgttcaacttcgtgccttgctccatctgctcc
aacaaccctacctgctgggccatctgcaagagaatccccaacaagaagcc
tggcaagaaaaccaccaccaagcctaccaagaagcctaccttcaagacca
ccaagaaggaccacaagcctcagaccacaaagcctaaggaagtgccaacc
accaagcaccaccaccatcaccactgataatcta Seq ID NO: 10
PreF_V2 peptide for CHO
MELLILKTNAITAILAAVTLCFASSQNITEEFYQSTCSAVSKGYLSALRT
GWYTSVITIELSNIKENKCNGTDAKVKLIKQELDKYKSAVTELQLLMQST
PATNNKKFLGFLLGVGSAIASGIAVSKVLHLECEVNKIKSALLSTNKAVV
SLSNGVSVLTSKVLDLKNYIDKQLLPIVNKQSCSISNIETVIEFQQKNNR
LLEITREFSVNAGVTTPVSTYMLTNSELLSLINDMPITNDQKKLMSNNVQ
IVRQQSYSIMSIIKEEVLAYVVQLPLYGVIDTPCWKLHTSPLCTTNTKEG
SNICLTRTDRGWYCDNAGSVSFFPLAETCKVQSNRVFCDTMNSLTLPSEV
NLCNIDIFNPKYDCKIMTSKTDVSSSVITSLGAIVSCYGKTKCTASNKNR
GIIKTFSNGCDYVSNKGVDTVSVGNTLYYVNKQEGKSLYVKGEPIINFYD

PLVFPSDEFDASISQVNEKINQSLAFIRKSDEKLHNVEDKIEEILSKIYH

IENEIARIKKLIGEAGGKQRQNKPPNKPNNDFHFEVFNFVPCSICSNNPT

CWAICKRIPNKKPGKKTTTKPTKKPTFKTTKKDHKPQTTKPKEVPTTK

SEQ ID NO: 11
Exemplary coiled-coil (isoleucine zipper)
EDKIEEILSKIYHIENEIARIKKLIGEA SEQ ID NO: 12
PreF antigen polynucleotide CHO2
atggagctgcccatcctgaagaccaacgccatcaccaccatcctcgccgc cgtgaccctgtgcttcgccagcagccagaacatcacggaggagttctacc agagcacgtgcagcgccgtgagcaagggctacctgagcgcgctgcgcacg ggctggtacacgagcgtgatcacgatcgagctgagcaacatcaaggagaa caagtgcaacggcacggacgcgaaggtgaagctgatcaagcaggagctgg acaagtacaagagcgcggtgacggagctgcagctgctgatgcagagcacg ccggcgacgaacaacaagttcctcggcttcctgctgggcgtgggcagcgc gatcgcgagcggcatcgccgtgagcaaggtgctgcacctggagggcgagg tgaacaagatcaagtccgcgctgctgagcacgaacaaggcggtcgtgagc ctgagcaacggcgtgagcgtgctgacgagcaaggtgctcgacctgaagaa ctacatcgacaagcagctgctgccgatcgtgaacaagcagagctgcagca tcagcaacatcgagaccgtgatcgagttccagcagaagaacaaccgcctg ctggagatcacgcgggagttctccgtgaacgcaggcgtgacgacgccgt gtctacgtacatgctgacgaacagcgagctgctcagcctgatcaacgaca tgccgatcacgaacgaccagaagaagctgatgagcaacaacgtgcagatc gtgcgccagcagagctacagcatcatgagcatcatcaaggaggaggtgct ggcatacgtggtgcagctgccgctgtacggcgtcatcgacacgccctgct ggaagctgcacacgagcccgctgtgcacgaccaacacgaaggagggcagc aacatctgcctgacgcggacggaccggggctggtactgcgacaacgcggg cagcgtgagcttcttcccgctcgcggagacgtgcaaggtgcagagcaacc gcgtcttctgcgacacgatgaacagcctgacgctgccgagcgaggtgaac ctgtgcaacatcgacatcttcaacccgaagtacgactgcaagatcatgac gagcaagaccgatgtcagcagcagcgtgatcacgagcctcggcgcgatcg tgagctgctacggcaagacgaagtgcacggcgagcaacaagaaccgcggc atcatcaagacgttcagcaacggctgcgactatgtgagcaacaagggcgt ggacactgtgagcgtcggcaacacgctgtactacgtgaacaagcaggagg gcaagagcctgtacgtgaagggcgagccgatcatcaacttctacgacccg ctcgtgttcccgagcgacgagttcgacgcgagcatcagccaagtgaacga gaagatcaaccagagcctggcgttcatccgcaagagcgacgagaagctgc acaacgtggaggacaagatcgaggagatcctgagcaagatctaccacatc gagaacgagatcgcgcgcatcaagaagctgatcggcgaggcgcatcatca ccatcaccattga SEQ ID NO: 13
PreF anitgen polynucleotide with intron
atggagctgctgatcctgaaaaccaacgccatcaccgccatcctggccgc cgtgaccctgtgcttcgcctcctcccagaacatcaccgaggagttctacc agtccacctgctccgccgtgtccaagggctacctgtccgccctgcggacc ggctggtacacctccgtgatcaccatcgagctgtccaacatcaaggaaaa caagtgcaacggcaccgacgccaaggtgaagctgatcaagcaggagctgg acaagtacaagagcgccgtgaccgaactccagctgctgatgcagtccacc cctgccaccaacaacaagtttctgggcttcctgctgggcgtgggctccgc catcgcctccggcatcgccgtgagcaaggtacgtgtcgggacttgtgttc ccctttttttaataaaaagttatatctttaatgttatatacatatttcct gtatgtgatccatgtgcttatgactttgtttatcatgtgtttaggtgctg cacctggagggcgaggtgaacaagatcaagagcgccctgctgtccaccaa caaggccgtggtgtccctgtccaacggcgtgtccgtgctgacctccaagg tgctggatctgaagaactacatcgacaagcagctgctgcctatcgtgaac aagcagtcctgctccatctccaacatcgagaccgtgatcgagttccagca gaagaacaaccggctgctggagatcacccgcgagttctccgtgaacgccg gcgtgaccaccctgtgtccacctacatgctgaccaactccgagctgctg tccctgatcaacgacatgcctatcaccaacgaccagaaaaaactgatgtc caacaacgtgcagatcgtgcggcagcagtcctacagcatcatgagcatca tcaaggagaggtgctggcctacgtggtgcagctgcctctgtacggcgtg atcgacaccccttgctggaagctgcacacctcccccctgtgcaccaccaa caccaaggagggctccaacatctgcctgacccggaccgaccggggctggt actgcgacaacgccggctccgtgtccttcttccctctggccgagacctgc aaggtgcagtccaacccgggtgttctgcgacaccatgaactccctgaccct gccttccgaggtgaacctgtgcaacatcgacatcttcaaccccaagtacg actgcaagatcatgaccagcaagaccgacgtgtcctccagcgtgatcacc tccctgggcgccatcgtgtcctgctacggcaagaccaagtgcaccgcctc caacaagaaccggggaatcatcaagaccttctccaacggctgcgactacg tgtccaataagggcgtggacaccgtgtccgtgggcaacacactgtactac gtgaataagcaggagggcaagagcctgtacgtgaagggcgagcctatcat caacttctacgaccctctggtgttccctcccacgagttcgacgcctcca tcagccaggtgaacgagaagatcaaccagtccctggccttcatccggaag tccgacgagaagctgcataacgtggaggacaagatcgaggagatcctgtc caaaatctaccacatcgagaacgagatcgcccggatcaagaagctgatcg gcgaggccggaggtcaccaccaccatcaccactga SEQ ID NO: 14
Synthetic linker sequence
GGSGGSGGS SEQ ID NO: 15
Furin cleavage site
RARR SEQ ID NO: 16
Furin cleavage site
RKRR

We claim:

1. A recombinant respiratory syncytial virus (RSV) antigen comprising an F2 domain and an F1 domain of an RSV F protein polypeptide with no intervening furin cleavage site wherein the polypeptide further comprises a heterologous trimerization domain positioned C-terminal to the $F_1$ domain.

2. The recombinant RSV antigen of claim 1, wherein the $F_2$ domain comprises at least a portion of an RSV F protein polypeptide corresponding to amino acids 26-105 of the reference F protein precursor polypeptide ($F_0$) of SEQ ID NO:2.

3. The recombinant RSV antigen of claim 1, wherein the $F_1$ domain comprises at least a portion of an RSV F protein polypeptide corresponding to amino acids 137-516 of the reference F protein precursor polypeptide ($F_0$) of SEQ ID NO:2.

4. The recombinant RSV antigen of claim 1, wherein the $F_2$ domain comprises an RSV F protein polypeptide corresponding to amino acids 26-105 and/or wherein the $F_1$ domain comprises an RSV F protein polypeptide corresponding to amino acids 137-516 of the reference F protein precursor polypeptide ($F_0$) of SEQ ID NO:2.

5. The recombinant RSV antigen of claim 1, wherein the RSV antigen is selected from the group of:
   a) a polypeptide comprising SEQ ID NO:6;
   b) a polypeptide with at least 80% sequence identity to SEQ ID NO:6, which polypeptide comprises an amino acid sequence corresponding to the RSV F protein polypeptide of a naturally occurring RSV strain;
   c) a polypeptide with at least 95% sequence identity to SEQ ID NO:6, which polypeptide comprises an amino acid sequence that does not correspond to a naturally occurring RSV strain,
   wherein the RSV antigen polypeptide maintains the characteristic of comprising no intervening furin cleavage site between the F2 domain and the F1 domain and comprising a heterologous trimerization domain.

6. The recombinant RSV antigen of claim 1, further comprising a signal peptide.

7. The recombinant RSV antigen of claim 1, wherein the heterologous trimerization domain comprises a coiled-coil domain.

8. The recombinant. RSV antigen of claim 7, wherein the heterologous trimerization domain comprises an isoleucine zipper.

9. The recombinant RSV antigen of claim 1, wherein the RSV antigen comprises at least one modification selected from:
   (i) a deletion of at least one non-furin cleavage site;
   (ii) a deletion of one or more amino acids of the pep27 domain; and
   (iii) at least one substitution or addition of a hydrophilic amino acid in a hydrophobic domain of the F protein extracellular domain.

10. The recombinant RSV antigen of claim 1, wherein the RSV antigen comprises a multimer of polypeptides.

11. The recombinant RSV antigen of claim 10, wherein the RSV antigen comprises a trimer of polypeptides.

12. An immunogenic composition comprising the recombinant RSV antigen of claim 1, and a pharmaceutically acceptable carrier or excipient.

13. The immunogenic composition of claim 12, wherein the carrier or excipient comprises a buffer.

14. The immunogenic composition of claim 12, further comprising an adjuvant

15. The immunogenic composition of claim 14, wherein the adjuvant comprises at least one of: 3D-MPL, QS21, an oil-in-water emulsion, and an aluminum or calcium salt.

16. The immunogenic composition of claim 12, wherein the immunogenic composition inhibits infection with Respiratory Syncytial Virus (RSV).

17. The immunogenic composition of claim 12, further comprising at least one additional antigen of a pathogenic organism other than RSV.

18. A method for eliciting an immune response against Respiratory Syncytial Virus (RSV), the method comprising:
    administering to a subject a composition comprising the immunogenic composition of claim 12.

19. The method of claim 18, wherein administering the composition comprising the RSV antigen elicits an immune response specific for RSV without enhancing viral disease following contact with RSV.

20. The immunogenic composition of claim 15, wherein the adjuvant comprises 3D-MPL and Alum.

* * * * *